(12) United States Patent
Fuchs et al.

(10) Patent No.: US 6,333,401 B1
(45) Date of Patent: Dec. 25, 2001

(54) PHENOL-INDUCED PROTEINS OF THAUERA AROMATICA

(75) Inventors: Georg Fuchs, Freiburg; Sabine Breinig, Freiburg Im Breigau, both of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/516,914

(22) Filed: Mar. 1, 2000

Related U.S. Application Data

(60) Provisional application No. 60/122,952, filed on Mar. 5, 1999.

(51) Int. Cl.$^7$ .............................. C07H 21/04; C12N 1/20; C12N 5/10; C12N 1/15
(52) U.S. Cl. ..................... 536/23.2; 435/252.3; 435/419; 435/325; 435/254.11
(58) Field of Search ........................ 536/23.2; 435/252.3, 435/419, 325, 254.11

(56) References Cited

PUBLICATIONS

Brackmann et al., Enzymes of anaerobic metabolism of phenolic compounds: 4–hydroxybenzoyl–CoA reductase (dehydroxylating) from a denitrifying Pseudomonas species, *European Journal of Biochemistry*, vol. 213, No. 1, pp. 563–571, 1993 XP000921140.

Heider et al., Differential induction of enzymes involved in anaerobic metabolism of aromatic compounds in the denitrifying bacterium Thauera aromatica, Archives of Microbiology, vol. 170, No. 2., pp. 120–131, Aug. 1998, XP000921128.

Dangel et al., Differential Expression of Enzyme Activities initiating Anoxic Metabolism of Various Aromatic Compounds Via Benzoyl Coenzyme A, *Archives of Microbiology*, vol. 155, No. 3, pp. 256–262, 1991, XP000921141.

Anders Hans–Joachim et al., Taxonomic position of aromatic–degrading denitrifying pseudomonad strains K 172 and KB 740 and their description oas new members of the genera Thauera, as Thauera aromatica sp. Nov., and Azoarcus, as Azoarcus evansii sp. nov., respectively, membersofthe beta subclass of Proteobacteria, International Journal of Systematic Bacteriology, vol. 45, No. 2, 1995 pp. 327–333, XP0020912945.

Aresta et al., Enzymatic Synthesis of 4–OH–Benzoic Acid from Phenol and CO2; the First Example of Biotechnological Application of a Carboxylase Enzyme, Tetrahendron, NL, Elsevier Science Publishers, Amsterdam, vol. 54, No. 30, Jul. 23, 1998 pp. 8841–8846, XP00412144049.

Takeo, M., Cloning and Sequencing of the regulation gene of the phenol degradative genes from Pseudomonas putida BH, EMBL Sequence Date Library, Aug. 25, 1995, XP002141705.

Blattner et al., The complete genome sequence of *Escherichia coli* K–12, EMBL Sequence Data Library, Mar. 1, 1989, XP002141706.

Zhang et al., *App. Environ. Microbiol.*, 63, 4759–4764, 1997.

Heider et al., *Eur. J. Biochem.*, 243, 577–596, 1997.

Winter et al., *Appl. Microbiol. Biotechnol*, 25, 384–391, 1987.

He et al., *Eur. J. Biochem*, 229, 77–82, 1995.

He et al., *J. Bacteriol.*, 178, 3539–3543, 1996.

Van Schie et al., *Appl. Environ. Microbiol.* 64, 2432–2438, 1998.

Tschech et al., *Arch. Microbiol.* 148, 213–217, 1987.

Lack et al., *Eur. J. Biochem.* 197, 473–479, 1991.

Lack et al., *Arch. Microbiol.* 161, 132–139, 1994.

Lack et al., *J.Bacteriol.* 174, 3629–3636, 1992.

*Primary Examiner*—Rebecca E. Prouty
*Assistant Examiner*—David J. Steadman

(57) ABSTRACT

This invention pertains to genes coding for phenol-induced proteins-Five phenol-induced proteins isolated from *Thauera aromatica*. Three dominant phenol-induced proteins called F1, F2, and F3 respectively were purified and sequenced to obtain the enzyme(s) that catalyze the $^{14}CO_2$:4-hydroxybenzoate isotope exchange reaction and the carboxylation of phenylphosphate. The N-terminal amino acid sequences of these proteins as well as the N-terminus of the phenol-induced proteins (F4 and F5) were also determined.

2 Claims, 13 Drawing Sheets

US 6,333,401 B1

PHENOL-INDUCED PROTEINS OF *THAUERA AROMATICA*

This application claims benefit of Provisional Application No. 60/122,952, filed Mar. 5, 1999.

FIELD OF THE INVENTION

This invention is in the field of molecular biology. More specifically, this invention pertains to nucleic acid fragments encoding phenol-induced proteins of the denitriying bacterium Thauera aromatics

BACKGROUND OF THE INVENTION

Phenolic compounds are basic chemicals of high interest to the chemical and pharmaceutical industries. Phenolic compounds are important plant constituents and phenol is formed from a variety of natural and synthetic substrates by the activity of microorganisms. The aerobic metabolism of phenol has been studied extensively; in all aerobic metabolic pathways oxygenases initiate the degradation of phenol by hydroxylation to catechol. Catechol can be oxygenolytically cleaved by dioxygenases, either by ortho- or meta-cleavage.

Anaerobic metabolism of phenol, aniline, o-cresol (2-methylphenol), hydroquinone (1,4-dihydroxybenzene), catechol (1,2-dihydroxybenzene), naphthalene and phenanthrene (Zhang et al., *App. Environ. Microbiol.* 63:4759–4764 (1997)) by denitrifying and sulfate-reducing bacteria involves carboxylation of the aromatic ring ortho orpara to the hydroxy or amino substituent. Products are 4-hydroxybenzoate, 4-aminobenzoate, 4-hydroxy-3-methylbenzoate, gentisate (2,5-dihydroxybenzoate), and protocatechuate (3,4-dihydroxybenzoate) (Heider et al., *Eur. J. Biochem.* 243:577–596 (1997)). Consortia of fermenting bacteria convert phenol to benzoate and decarboxylate 4-hydroxybenzoate to phenol (Winter et al., *Appl. Microbiol. Biotechnol.* 25:384–391 (1987); He et al., *Eur. J. Biochem.* 229:77–82 (1995); He et al., *J. Bacteriol.* 178:3539–3543 (1996); Van Schie et al., *Appl. Environ. Microbiol.* 64:2432–2438 (1998)). They also catalyze an isotope exchange between $D_2O$ and the proton at C4 of the aromatic ring of 4-hydroxybenzoate. Phenol carboxylation to 4-hydroxybenzoate in the denitritying bacterium *Thauera aromatica* is the best studied of these carboxylation reactions and is a paradigm for this new type of carboxylation reaction (Tschech et al., *Arch. Microbiol.* 148:213–217 (1987); Lack et al., *Eur. J. Biochem.* 197:473–479 (1991); Lack et al., *J. Bacteriol.* 174:3629–3636 (1992); Lack et al., *Arch. Microbiol.* 161:132–139 (1994)).

Without an isolated gene and corresponding sequence of the coding sequence, there remains a need for a convenient way to produce various intermediates in phenol metabolism with a transformed microorganism.

SUMMARY OF THE INVENTION

Five phenol-induced proteins from *Thauera aromnatica* have been isolated. Three dominant phenol-induced proteins called F1, F2, and F3 were purified and sequenced in an attempt to purif the enzyme(s) that catalyze the $^{14}CO_2$:4-hydroxybenzoate isotope exchange reaction and the carboxylation of phenylphosphate. The N-terminal amino acid sequences of these proteins as well as the N-terminus of the phenol-induced proteins F4 and F5 were determined. Internal sequences of F2 were obtained by trypsin digest. All of these sequences have application in industrial processes that involve the use of phenol or its intermediates. The instant invention provides a means to manipulate phenol metabolism and to produce various phenol intermediates in recombinant micro-organisms. The approach is based on the observation that anoxic growth with phenol and nitrate induces novel proteins that are lacking in cells grown with 4-hydroxybenzoate and nitrate.

BRIEF DESCRIPTION OF THE SEQUENCE DESCRIPTIONS

The following 44 sequence descriptions and sequence listings attached hereto comply with the rules governing nucleotide and/or amino acid sequence disclosures in patent applications as set forth in 37 C.F.R. §1.821–1.825 ("Requirements for Patent Applications contaning nucleotide sequences and/or Amino Acid Sequence Disclosure— the Sequence Rules") and consistent with World Intellectual Property Organization (WIPO) Standard ST.25 (1998) and the sequence listing requirements of the EPO and PCT (Rules 5.2 and 4.95(a-bis) and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219(2):345–373 (1984) which are herein incorporated by reference. The symbols and format used for nucleotide and amino acid sequence data comply with the rules set forth in 37 C.F.R. §1.822. The present invention utilizes Wisconsin Package Version 9.0 software from Genetics Computer Group (GCG), Madison, Wis.

SEQ ID NO:1 is the deduced amino acid sequence of protein F1 and is coded by orf6.

SEQ ID NO:2 is the nucleotide sequence of orf6 that codes for protein F1.

SEQ ID NO:3 is the deduced amino acid sequence of protein F2 and is coded by orf4.

SEQ ID NO:4 is the nucleotide sequence of orf4 that codes for protein F2.

SEQ ID NO:5 is the deduced amino acid sequence of protein F3 and is coded by orf1.

SEQ ID NO:6 is the nucleotide sequence of orf1 that codes for protein F3.

SEQ ID NO:7 is the deduced amino acid sequence of protein F4 and is coded by orf5.

SEQ ID NO:8 is the nucleotide sequence of orf5 that codes for protein F4.

SEQ ID NO:9 is the deduced amino acid sequence of protein F5 and is coded by orf8.

SEQ ID NO:10 is the nucleotide sequence of orf8 that codes for protein F5.

SEQ ID NO:11 is the deduced amino acid sequence of orf2.

SEQ ID NO:12 is the nucleotide sequence of orf2 that codes for an unknown protein.

SEQ ID NO:13 is the deduced amino acid sequence of orf3.

SEQ ID NO:14 is the nucleotide sequence of orf3 that codes for an unknown protein.

SEQ ID NO:15 is the deduced amino acid sequence of orf7.

SEQ ID NO:16 is the nucleotide sequence of orf7 that codes for an unknown protein.

SEQ ID NO:17 is the deduced amino acid sequence of orf9.

SEQ ID NO:18 is the nucleotide sequence of orf9 that codes for an unknown protein.

SEQ ID NO:19 is the deduced amino acid sequence of orf10.

SEQ ID NO:20 is the nucleotide sequence of orf10 that codes for an unknown protein.

SEQ ID NO:21 is the deduced amino acid sequence of orf-1.

SEQ ID NO:22 is the nucleotide sequence of orf-1 that codes for an unknown protein.

SEQ ID NO:23 is the nucleotide sequence containing two gene clusters that are involved in phenol metabolism.

SEQ ID NO:24 is the N-terminal amino acid sequence of F1 (experimentally determined).

SEQ ID NO:25 is the N-terminal amino acid sequence of F1 (deduced from the genes).

SEQ ID NO:26 is the N-terminal amino acid sequence of F2 (experimentally determined).

SEQ ID NO:27 is the N-terminal amino acid sequence of F2 (deduced from the genes).

SEQ ID NO:28 is the N-terminal amino acid sequence of F3 (experimentally determined).

SEQ ID NO:29 is the N-terminal amino acid sequence of F3 (deduced from the genes).

SEQ ID NO:30 is the amino acid sequence of an internal fragment of F2 that was obtained by trypsin-digest.

SEQ ID NO:31 is the amino acid sequence of an internal fragment of F2 that was obtained by trypsin-digest.

SEQ ID NO:32 is the primer of F2-forward (N-terminus).

SEQ ID NO:33 is the primer of F2T6-reverse.

SEQ ID NO:34 is the primer of F2T43-reverse.

SEQ ID NO:35 is the primer T7.

SEQ ID NO:36 is the primer T3.

SEQ ID NO:37 is the primer designated breib31.

SEQ ID NO:38 is the primer designated breib07r3.

SEQ ID NO:39 is the primer of λ15-forward.

SEQ ID NO:40 is the primer of λ15-reverse.

SEQ ID NO:41 is the N-terminal amino acid sequence of F4 (experimentally determined).

SEQ ID NO:42 is the N-terminal amino acid sequence of F4 (deduced from the genes).

SEQ ID NO:43 is the N-terminal amino acid sequence of F5 (experimentally determined).

SEQ ID NO:44 is the N-terminal amino acid sequence of F5 (deduced from the genes).

DETAILED DESCRIPTION OF THE INVENTION

Figure 1:
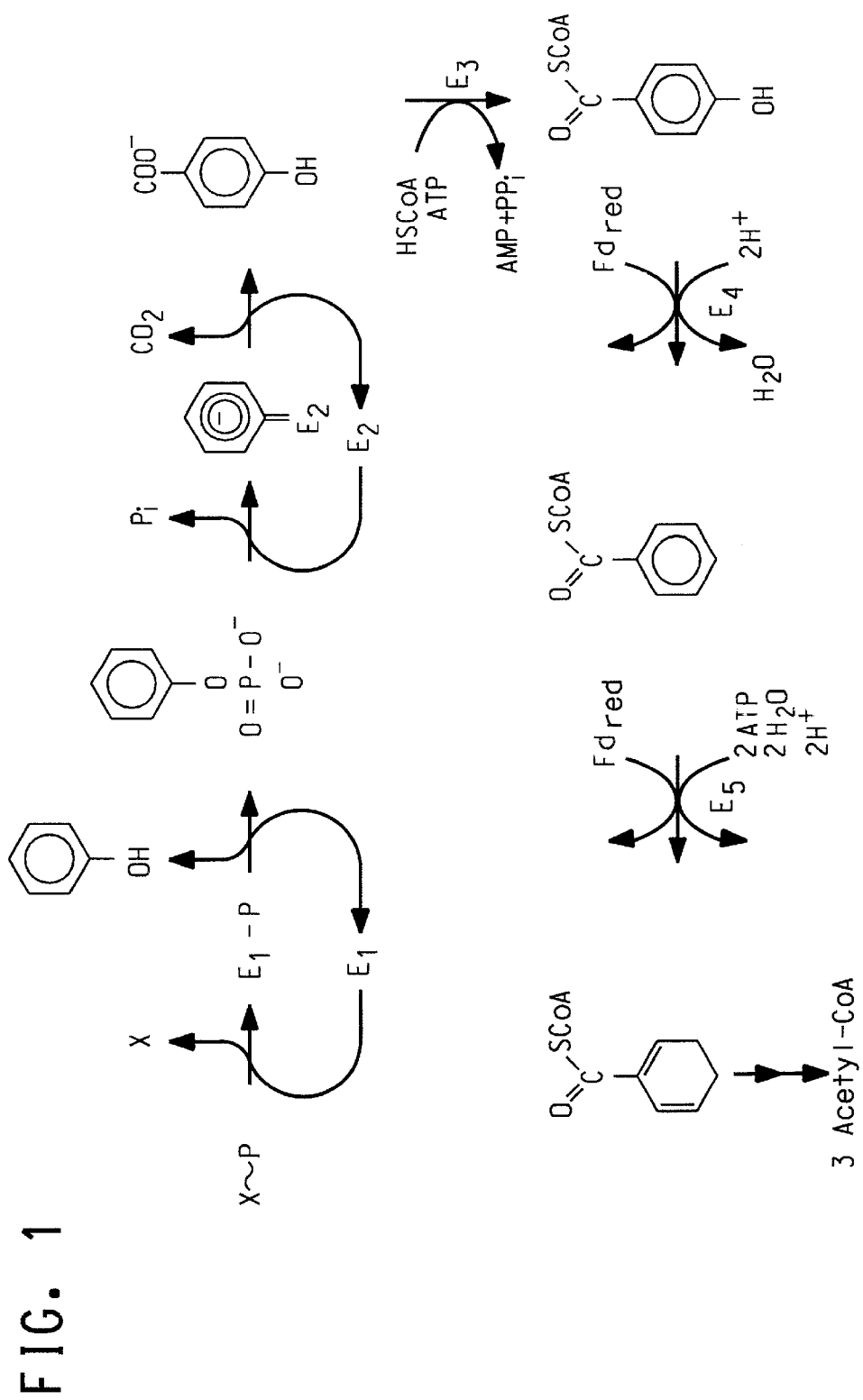
FIG. 1 shows phenol metabolism in *Thauera aromatica*. The enzymes active in this pathway are Phenylphosphate synthase $E_1$); Phenylphosphate carboxylase ($Mn^{2+}$, $K^+$)($E_2$); 4-Hydroxybenzoate-CoA Ligase ($E_3$); 4-Hydroxybenzoyl-CoA reductase (Mo, FAD, Fe/S) ($E_4$); Benzoyl-CoA reductase (Fe/S, FAD) ($E_5$).

Applicants have succeeded in identifying the genes coding for phenol-induced proteins. Five phenol-induced proteins from *Thauera aromatica* have been isolated. Three dominant phenol-induced proteins called F1, F2, and F3 were purified and sequenced to obtain the enzyme(s) that catalyze the $^{14}CO_2$:4-hydroxybenzoate isotope exchange reaction and the carboxylation of phenylphosphate. The N-terminal amino acid sequences of these proteins as well as the N-terminus of the phenol-induced proteins F4 and F5 were determined. Internal sequences of F2 were obtained by trypsin digest. All of these sequences have utility in industrial processes. The instant invention provides a means to manipulate phenol metabolism and specifically the carboxylation of phenyl phosphate. Transformation of host cells with at least one copy of the identified genes under the control of appropriate promoters will provide the ability to produce various intermediates in phenol metabolism. The approach is based on the observation that anoxic growth with phenol and nitrate induces novel proteins that are lacking in cells grown with 4-hydroxybenzoate and nitrate.

The following definitions are provided for the full understanding of terms and abbreviations used in this specification.

The abbreviations in the specification correspond to units of measure, techniques, properties, or compounds as follows: "sec" means second(s), "min" means minute(s), "h" means hour(s), "d" means day(s), "L" means microliter, "mL" means milliliters, "L" means liters, "mM" means millimolar, "M" means molar, "mmol" means millimole(s), "Ampr" means ampicillin resistance, "Amps" means ampicillin sensitivity, "kb" means kilo base, "kd" means kilodaltons, "m" means nanometers, and "wt" means weight. "ORF" means "open reading frame, "PCR" means polymerase chain reaction, "HPLC" means high performance liquid chromatography, "ca" means approximately, "dcw" means dry cell weight, "O.D." means optical density at the designated wavelength, "IU" means International Units.

"Polymerase chain reaction" is abbreviated PCR.

"Open reading frame" is abbreviated ORF.

"Sample channels ratio" is abbreviated SCR.

"High performance liquid chromatography" is abbreviated HPLC.

The term "F1" refers to the protein encoded by orf6.

The term "F2" refers to the protein encoded by orf4.

The term "F3" refers to the protein encoded by orf1.

The term "F4" refers to the protein encoded by orf5.

The term "F5" refers to the protein encoded by orf8.

The term "$E_1$" refers to phenol phosphorylating, phenol kinase or phenylphosphate synthase. Phenol phosphorylating and phenol kinase are used interchangeably by those skilled in the art.

The term "$E_2$" refers to phenylphosphate carboxylase.

The terms "isolated nucleic acid fragment" or "isolated nucleic acid molecule" refer to a polymer of mononucleotides (RNA or DNA) that is single- or double-stranded, optionally containing synthetic, non-natural or altered nucleotide bases. An isolated nucleic acid fragment or an isolated nucleic acid molecule in the form of a polymer of mononucleotides may be comprised of one or more segments of cDNA, genomic DNA, or synthetic DNA.

The terms "host cell" and "host microorganism" refer to a cell capable of receiving foreign or heterologous genes and expressing those genes to produce an active gene product. The term "suitable host cells" encompasses microorganisms such as bacteria and fungi, and also includes plant cells.

The term "fragment" refers to a DNA or amino acid sequence comprising a subsequence of the nucleic acid sequence or protein of the instant invention. However, an active fragment of the instant invention comprises a sufficient portion of the protein to maintain activity.

The term "gene cluster" refers to genes organized in a single expression unit or in close proximity to each other on the chromosome.

The term "substantially similar" refers to nucleic acid fragients wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that alterations in a gene which result in the production of a chemically equivalent amino acid at a given site, and yet do not effect the functional properties of the encoded protein, are common. For example, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a finctionally equivalent product. Nucleotide changes which result in alteration of the N-terminal and C-terminal portions of the protein molecule would also not be expected to alter the activity of the protein. Each of the proposed modifications is well within the routine skill in the art, as is determining what biological activity of the encoded products is retained. Moreover, the skilled artisan recognizes that substantially similar sequences encompassed by this invention are also defmed by their ability to hybridize, under stringent conditions (0.1xSSC, 0.1% SDS, 65° C. and washed with 2xSSC, 0.1% SDS followed by 0.1xSSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratora Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5xSSC, 0.1% SDS, 0.25% milk, and no formamide; or 30% formamide, 5xSSC, 0.5% SDS. Moderate stringency hybridization conditions correspond to a higher Tm, e.g., 40–45% formamide, with 5x or 6xSSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides (generally 12 bases or longer) may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

For example, it is well known in the art that antisense suppression and co-suppression of gene expression may be accomplished using nucleic acid fragments representing less than the entire coding region of a gene, and by nucleic acid fragments that do not share 100% identity with the gene to be suppressed. Moreover, alterations in a gene that result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.) or moderately stringent conditions, with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informnatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorthm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. USA* 85:2444–2448 (1988). The BLASTX program is publicly available from NCBI and other sources (*BLAST Manual*, Altschul et al., *Natl. Cent. Biotechnol. Inf., Natl. Library Med.* (NCBI NLM) NIH, Bethesda, Md. 20894; Altschul et al., *J. Mol. Biol.* 215:403–410 (1990); Altschul et al., "Gapped BLAST and PSI-BLAST: a new generation of protein database search programs", *Nucleic Acids Res.* 25:3389–3402 (1997)). The method to determine percent identity preferred in the instant invention is by the method of DNASTAR protein alignment protocol using the Jotun-Hein algorithm (Hein et al., *Methods Enzymol.* 183:626–645 (1990)). Default parameters used for the Jotun-Hein method for alignments are: for multiple alignments, gap penalty=11, gap length penalty=3; for pairwise alignments ktuple=2. As an illustration, for a polynucleotide having a nucleotide sequence with at least 95% "identity" to a reference nucleotide sequence, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, for a polypeptide having an amino acid sequence having at least 95% identity to a reference amino acid sequence, it is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant *Thauera aromatica* proteins as set forth in SEQ ID NO:1, SEQ ID NO:3 and SEQ ID NO:5. The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available.

"Gene" refers to a nucleic acid fragment that expresses a specific protein, including regulatory sequences preceding (5' noncoding sequences) and following (3' non-coding sequences) the coding sequence. "Native gene" refers to a gene as found in nature with its own regulatory sequences. "Chimeric gene" refers to any gene, not a native gene, comprising regulatory and coding sequences that are not found together in nature. Accordingly, a chimeric gene may compnse regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or finctional RNA. In general, a coding sequence is located 3' to a promoter sequence. The promoter sequence consists of proximal and more distal upstream elements, the latter elements often referred to as enhancers. An "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochemistry of Plants* 15:1–82 (1989)). It is firther recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fuilly processed mRNA upstream of the translation start sequence. The translation leader sequence may affect processing of the primary transcript to mRNA, mRNA stability or translation efficiency. Examples of translation leader sequences have been described (Turner et al., *Mol. Biotech*. 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript. The RNA transcript it may be a RNA sequence derived from posttranscriptional processing of the primary transcript and is referred to then as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or rnRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated, yet has an effect on cellular processes.

The term "operably-linked" refers to the association of nucleic acid sequences on a single nucleic acid fragment so that the function of one is affected by the other. For example, a promoter is operably-linked with a coding sequence when it affects the expression of that coding sequence (i.e., that the coding sequence is under the transcriptional control of the promoter). Coding sequences can be operably-linked to regulatory sequences in sense or antisense orientation.

The term "expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformned organisms. "Co-suppression" refers to the production of sense RNA transcripts capable of suppressing the expression of identical or substantially similar foreign or endogenous genes (U.S. Pat. No. 5,231,020).

"Altered level" refers to the production of gene product(s) in organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth. Enzymol.* 143:277 (1987)) and particle-accelerated or "gene gun" transformation technology (Klein et al., *Nature, London* 327:70–73 (1987); U.S. Pat. No. 4,945,050).

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Novel phenol-induced proteins, F1, F2, and F3, have been isolated. Comparison of their random cDNA sequences to the GenBank database using the BLAST algorithms, well known to those skilled in the art, revealed that F3 (orf1) and orf2 are proteins homologous to phosphoenolpyruvate sythase (PEP) of *E. coli* and are likely to represent the phenol phosphorylating enzyme $E_1$ (FIG. 1). The nucleotide sequences of the F1, F2, and F3 genomic DNA are provided in SEQ ID NO:2, SEQ ID NO:4, and SEQ ID NO:6, and their deduced amino acid sequences are provided in SEQ ID NO:1, SEQ ID NO:3, and SEQ ID NO:5, respectively. F1, F2, and F3 genes from other bacteria can now be identified by comparison of random cDNA sequences to the F1, F2, and F3 sequences provided herein.

The nucleic acid fragments of the instant invention may be used to isolate cDNAs and genes encoding homologous F1, F2, and F3 phenol-induced proteins from the same or other plant or fingal species. Isolating homologous genes using sequence-dependent protocols is well known in the art. Examples of sequence-dependent protocols include, but are not limited to, methods of nucleic acid hybridization and methods of DNA and RNA amplification as exemplified by various uses of nucleic acid amplification technologies (e.g., polymerase chain reaction (PCR) or ligase chain reaction).

For example, other F1, F2, and F3 genes, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant F1, F2, and F3 sequences can be designed and synthesized by methods known in the art (Sambrook, supra). Moreover, entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or fill-length of the instant sequences. The resulting amplification products can be labeled directly during amplification reactions or labeled after amplification reactions, and used as probes to isolate fuill length cDNA or genomic fragments under conditions of appropriate stringency.

In addition, two short segments of the instant ORF's may be used in PCR protocols to amplify longer nucleic acid fragments encoding homologous F1, F2, F3, F4, and F5 genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding bacterial F1, F2, F3, F4, and F5. Alternatively, the second primer sequence may be based upon sequences derived from the cloning vector. For example, the skilled artisan can follow the RACE protocol (Frohman et al., *Proc.*

*Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen cDNA expression libraries to isolate full-length cDNA clones of interest (Lerner et al., *Adv. Immunol.* 36:1(1984); Sambrook, supra).

The enzymes and gene products of the instant ORF's may be produced in heterologous host cells, particularly in the cells of microbial hosts, and can be used to prepare antibodies to the resulting proteins by methods well known to those skilled in the art. The antibodies are useful for detecting the proteins in situ in cells or in vitro in cell extracts. Preferred heterologous host cells for production of the instant enzymes are microbial hosts and include those selected from the following: Comamonas sp., Corynebacterium sp., Brevibacterium sp., Rhodococcus sp., Azotobacter sp., Citrobacter sp., Enterobacter sp., Clostridium sp., Klebsielia sp., Salmonella s.p, Lactobacillus sp., Aspergillus sp., Saccharonryces sp., Zygosaccharomyces sp , Pichia sp., Kluyveromyces sp., Candida sp., Hansenula sp., Dunaliella sp., Debaryomyces sp., Mucor sp., Torylopsis sp., Methylobacteriasp., Bacillussp., Escherichia sp., Pseudomonas sp., Rhizobium sp., and Streptomyces sp. Microbial expression systems and expression vectors containing regulatory sequences that direct high level expression of foreign proteins are well known to those skilled in the art. Any of these could be used to construct chimeric genes for production of any of the gene products of the instant ORF's. These chimeric genes could then be introduced into appropriate microorganisms via transformation to provide high level expression of the enzymes.

Additionally, chimeric genes will be effective in altering the properties of the host bacteria It is expected, for example, that introduction of chimeric genes encoding one or more of the ORF's 1–10 under the control of the appropriate promoters, into a host cell comprising at least one copy of these genes will demonstrate the ability to produce various intermediates in phenol metabolism. For example, the appropriately regulated ORF 1 and ORF 2, would be expected to express an enzyme capable of phosphorylating phenol (phenylphosphate synthase—FIG. 1). Similarly, ORF 4, ORF 6, ORF 7 and ORF 8 would be expected to express an enzyme capable of carboxylating phenylphosphate to afford 4-hydroxbenzoate (phenylphosphate carboxylase—FIG. 1). Finally, expression of SEQ ID NO:23 in a single recombinant organism will be expected to effect the conversion of phenol to 4-hydroxybenzoate in a transformed host (FIG. 1).

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. A promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *Escherichia coli*). Useful strong promoters may also be used from Corynebacterium, Comamonas, Pseudomonas, and Rhodococcus.

Termination control regions may also be derived from various genes native to the preferred hosts. Optionally, a termination site may be unnecessary, however, it is most preferred if included.

Description of the Preferred Embodiments

In the denitrifying bacterium Thauera aromatica phenol carboxylation proceeds in two steps and involves formation of phenylphosphate as the first intermediate (Equation 1). Cells grown with phenol were simultaneously adapted to growth with 4-hydroxybenzoate, whereas, vice-versa, 4-hydroxybenzoate-grown cells did not metabolize phenol. Induction of the capacity to metabolize phenol required several hours.

An enzyme activity catalyzing an isotope exchange of the phenyl moiety of phenylphosphate with free $^{14}C$-phenol was identified in extracts of phenol-grown cells (Equation 2), and was lacking in 4-hydroxybenzoate grown cells. Free $^{32}P$-phosphate did not exchange with phenylphosphate. This suggests a phosphorylated enzyme $E_1$ (Equations 3 and 4) which becomes phosphorylated in an essentially irreversible step (Equation 5). The phosphorylated enzyme transforms phenol to phenylphosphate in a reversible reaction (Equation 6). The whole reaction is understood as the sum of Equation 5 and Equation 6. The phosphoryl donor X~P is unknown so far. The enzyme $E_1$ is termed phenol kinase.

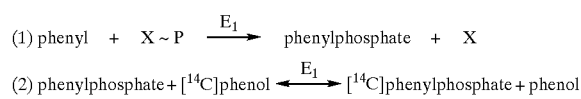

(1) phenyl + X~P $\xrightarrow{E_1}$ phenylphosphate + X (2) phenylphosphate + [$^{14}C$]phenol $\xleftrightarrow{E_1}$ [$^{14}C$]phenylphosphate + phenol

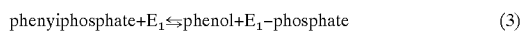

phenylphosphate+$E_1$⇌phenol+$E_1$–phosphate (3)

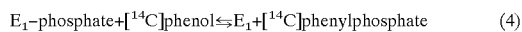

$E_1$–phosphate+[$^{14}C$]phenol⇌$E_1$+[$^{14}C$]phenylphosphate (4)

X~P+$E_1$→$E_1$–phosphate+X (5)

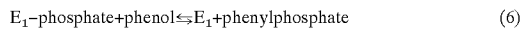

$E_1$–phosphate+phenol⇌$E_1$+phenylphosphate (6)

Phenylphosphate is the substrate of a second enzyme $E_2$, phenylphosphate carboxylase. It requires $K^+$ and $Mn^{2+}$ and catalyzes the carboxylation of phenylphosphate to 4-hydroxybenzoate (Equation 7). An enzyme activity catalyzing an isotope exchange between the carboxyl of 4-hydroxybenzoate and free $^{14}CO_2$ (Equation 8) was present in phenol-grown cells. Free $^{14}C$-phenol did not exchange. This suggests an enzyme $E_2$-phenolate intermediate (Equations 9 and 10) which is formed in a presumably exergonic reaction (Equation 11) followed by the reversible carboxylation (Equation 12). The actual substrate is $CO_2$ rather than bicarbonate, and the carboxylating enzyme was not inhibited by avidin; both results suggest that biotin is not involved in carboxylation. The enzyme $E_2$ is termed phenylphosphate carboxylase.

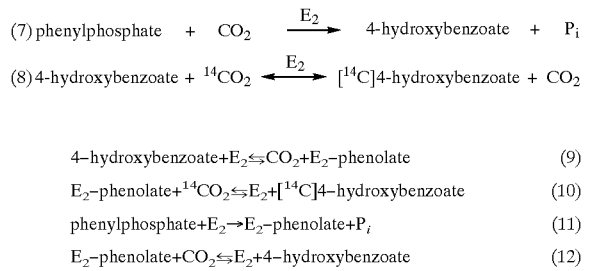

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard recombinant DNA and molecular cloning techniques used here are well known in the art and are described by Sambrook, J., Fritsch, E. F. and Maniatis, T. *Molecular Cloring: A Labortory Manual*, Cold Spring Harbor Laboratory Press, Cold Spring Harbor, 1989 (hereinafter "Sambrook"); and by T. J. Silhavy, M. L. Bennan, and L. W. Enquist, *Experiments with Gene Fusions*, Cold Spring Harbor Laboratory Press, Cold Spring, N.Y. (1984) and by Ausubel et al., *Current Protocols in Molecular Biology*, pub. by Greene Publishing Assoc. and Wiley-Interscience (1987).

Manipulations of genetic sequences were accomplished using the suite of programs available from the Genetics Computer Group Inc. (Wisconsin Package Version 9.0, Genetics Computer Group (GCG), Madison, Wis.) and PC/Gene©: the nucleic acid and protein sequence analysis software system, A. Bairoch, University of Geneva, Switzerland, Intelligenetics™ Inc. Serial Number IGI2626/ Version 6.70; programs used were as follows: REFORM— sequence file conversion program, Version 4.3, February 1991; RESTRI—restriction site analysis; NMANIP— simple nucleic acid sequence manipulations (inverse and complement the sequence); HAIRPIN—search for hairpin loops in a nucleotide sequence; default parameters: rminimum stem size: 5, lower range of number of unpaired bases: 3, upper range of number of unpaired bases: 20, allowed basepairs: G-C, A-T (A-U).

Example 1

Strains and Culture Conditions

In the denitdwing bacterium Thauera aromatica phenol carboxylation proceeds in two steps and involves formation of phenylphosphate as the first intermediate (FIG. 1). Cells grown with phenol were simultaneously adapted to growth with 4hydroxybenzoate, whereas, vice-versa, 4-hydroxybenzoate-grown cells did not metabolize phenol. Induction of the capacity to metabolize phenol required several hours. The enzyme system not only acts on 4-hydroxy-benzoate/phenol (100%), but also on protocatechuate/catechol (30%), o-cresol (30%), 2-chlorophenol (75%) and 2,6-dichlorophenol (30%). The enzyme specifically catalyzes a para-carboxylation, and anaerobic growth of the organism on phenolic compounds and nitrate requires $CO_2$.

Both, the phosphorylating and the carboxylating enzymes ($E_1$ and $E_2$, respectively), are strictly regulated. All activities were only present after anoxic growth of cells on phenol, and were lacking after growth on 4-hydroxybenzoate. Further metabolism of 4-hydroxybenzoate proceeds via benzyl-CoA in two steps, as shown in FIG. 1.

*Thauera aromatica* (K 172) was cultured anaerobically at 30° C. in a mineral salt medium (1.08 g/L $KH_2PO_4$, 5.6 g/L $K_2HPO_4$, 0.54 g/L $NH_4Cl$) supplemented with 0.1 mM $CaCl_2$, 0.8 mM $MgSO_4$, 1 mL/L vitamin solution (cyanocobalamin 100 mg/L, pyridoxamin-2 HCl 300 mg/L, Ca-D(+)-pantothenate 100 mg/L, thiamindichloride 200 mg/L, nicotinate 200 mg/L, 4-aminobenzoate 80 mg/L, D(+)-biotin 20 mg/L) and 1 mL/L of a solution of trace elements (25% HCl 10 mL/L, $FeCl_2.4H_2O$ 1.5 g/l, $ZnCl_2$ 70 mg/L, $MnCl_2.4H_2O$ 100 mg/L, $CoCl_2.6H_2O$ 100 mg/L, $CuCl_2.2H_2O$ 2 mg/L, $NiCl_2.6H_2O$ 24 mg/L, $Na_2MoO_4.2H_2O$ 36 mg/L, $H_3BO_3$ 6 mg/L). 0.5 mM phenol and 10 mM $NaHCO_3$ as sole source of carbon and energy were added, as well as 2 mM $NaNO_3$ as the terminal electron acceptor. Note: All media, supplements and substrates were strictly anaerobic.

*Escherichia coli* strains XL1-blue [(F', proAB, lacIqZΔM15, Tn10, tet$^R$), gyrA96, hsdR17, recA1, relA1, thi-1, Δ(lac), Lambda$^-$], K38 [hfrC, ompF267,phoA4, pit-10, relA1] and P2392 [hsdR514, supE44, supF58, lacY1, galK2, galT22, met1, trpR55, mcrA, P2 lysogen] were cultured in Luria-Bertani medium at 37° C. (Sambrook). Antibiotics were added to *E. coli* cultures to the following final concentrations: kanamycin 50 μg/mL, ampicillin 50 μg/mL and tetracycline 20 μg/mL.

Example 2

4-Hydroxybenzoate:$^{14}CO_2$-Isotope Exchange

The assay conditions were as follows: 20 mM imidazole/ HCl (pH 6.5), 20 mM KCl, 0.5 mM $MnCl_2$, 2 mM 4-hydroxybenzoate, 50 μmol $CO_2$ (50 μL 1 M $NaHCO_3$ per 1 nL assay), 25 μL soluble fraction (see Example 4) per 1 mL assay. The reaction was started by addition of 10 μL $^{14}C$-$Na_2CO_3$ (7 kBq; specific radioactivity 80 nCi/mmol). After 5 min incubation at 30° C. the reaction was stopped by the addition of 30 μL 3 M perchloric acid per 250 μL sample. The precipitated proteins were centrifuged down and the supernatant was acidified with 150 μL 10 M formic acid. The mixture was incubated under steady flow of $CO_2$ (10 MnL/ min) to remove all the $^{14}CO_2$ which was not fixed in the reaction. After 15 min 150 μL 1 M $KHCO_3$ was added and incubated another 15 min under steady flow of $CO_2$ (10 mL/min). The formed amount of non-volatile labeled product (4-hydroxybenzoate:$^{14}CO_2$) was analyzed by liquid scintillation counting.

Measurement of the 4-hydroxybenzoate:$^{14}CO_2$-isotope exchange in the soluble fraction of cells grown on phenol and 4-hydroxybenzoate, respectively was performed in an assay described below:

| | |
|---|---|
| 50 mM MnCl$_2$ | 10 µL |
| 2M KCl | 10 µL |
| 1M NaHCO$_3$ | 50 µL |
| 0.2M 4-hydroxybenzoate | 10 µL |
| 20 mM imidazole/HCl pH 6.5 | 895 µL |
| soluble fraction | 25 µL |
| 14C-Na$_2$CO$_3$ | 10 µL (≈3923 Bq) |

Following incubation for 4 min /30° C., to 200 µL sample treated as described above, 3.0 mL of scintillation cocktail was added and the amount of 14C was counted in a liquid scintillation counter for 5 min. The output of the scintillation counter was:

| sample | CpmA | cpmB | scr** | dpmA | dpmB | % A* | % B* |
|---|---|---|---|---|---|---|---|
| Phenol grown cells | 276 | 1659 | 0.168 | 0 | 1900 | .00 | 87.32 |
| 4-hydroxy-benzoate grown cells | 6 | 20 | 0.318 | 0 | 25 | .00 | 79.44 |
| no cell extract (control) | 5 | 11 | 0.386 | 0 | 15 | .00 | 75.97 |

*A and B stand for the two windows in which the counting takes place and are preset for $^{14}$C. The results are reliable when % B is about 75% or higher.
**scr stands for Sample Channels Ratio method and it relates to the efficiency and reliability of the measurements (a scr value of about 0.1–0.25 is optimal).

Calculating of the activity (nmol min$^{-1}$ mg$^{-1}$): total incorporation of $^{14}$CO$_2$ would result in a value of 235380 dpm (desintegrations per minute, 60×3923 Bq) per 50 µmoL NaHCO$_3$ in 1 mL assay. 1900 dpm (see table dpmB) correspond to 32 Bq which means 382 nmol/4 min×200 µL sample. A 200 µL sample contains about 5 µL soluble fraction. The protein concentration of the soluble fraction of phenol-grown cells is about 62 mg/mL. Therefore, a 200 µL of sample corresponds to 310 µg soluble fraction. The specific activity was determined to be 308 nmol/min·mg protein.

Example 3

Carboxylation of Phenylphosphate

Phenylphosphate is the substrate of the second enzyme E$_2$, phenylphosphate carboxylase. It requires K$^+$ and Mn$_{2+}$ and catalyzes the carboxylation of phenylphosphate to 4-hydroxybenzoate. The assay conditions were as follows: 20 mM imidazole/HCl (pH 6.5), 20 mM KCl, 0.5 mM MnCl$_2$, 2 mM phenylphosphate, 25 µmol CO$_2$ (25 µL 1 M NaHCO$_3$ per 1 mL assay), 25 µL soluble fraction (see Example 4) per 1 mL assay. The reaction was started by addition of 20 µL $^{14}$C-Na$_2$CO$_3$ (14 kBq; specific radioactivity 250 nCi/mmol). After 5 min incubation at 30° C. the reaction was stopped by the addition of 30 µL 3 M perchloric acid per 250 µL sample. The precipitated proteins were centrifuged down and the supernatant was acidified with 150 µL 10 M formic acid. The mixture was incubated under steady flow of CO$_2$ (10 mL/min) to remove all the $^{14}$CO$_2$ which was not fixed in the reaction. After 15 min 150 µL of 1.0 M KHCO$_3$ was added and incubated another 15 min under steady flow of CO$_2$ (10 mL/min). The formed amount of non-volatile labeled product was analyzed by liquid scintillation counting.

See description in Example 2 with the difference that 0.2 M phenyl-phosphate instead of 4-hydroxybenzoate and 25 µL 1 M NaHCO$_3$ instead of 50 µL were used. The output of the scintillation counter was:

| sample | cpmA | cpmB | scr** | dpmA | dpmB | % A* | % B* |
|---|---|---|---|---|---|---|---|
| phenol | 21 | 114 | 0.199 | 0 | 134 | .00 | 85.65 |
| 4-hydroxy-benzoate | 7 | 19 | 0.360 | 0 | 24 | .00 | 77.28 |
| no extract | 5 | 11 | 0.386 | 0 | 15 | .00 | 75.97 |

*A and B stand for the two windows in which the counting takes place and are preset for $^{14}$C. The results are reliable when % B is about 75% or higher.
**scr stands for Sample Channels Ratio method and it relates to the efficiency and reliability of the measurements (a scr value of about 0.1–0.25 is optimal).

The carboxylase activity was calculated as described in Example 2 taking into account the fact that 3923 Bq (235380 dpm) =25 µmol incorporated $^{14}$CO$_2$ per 1 mL assay. The specific activity was determined to be 10 nmol/min/mg.

Example 4

Partial Purification and Amino Acid Sequencing of Three Dominant Phenol-Induced Proteins F1, F2 and F3

Figure 2:
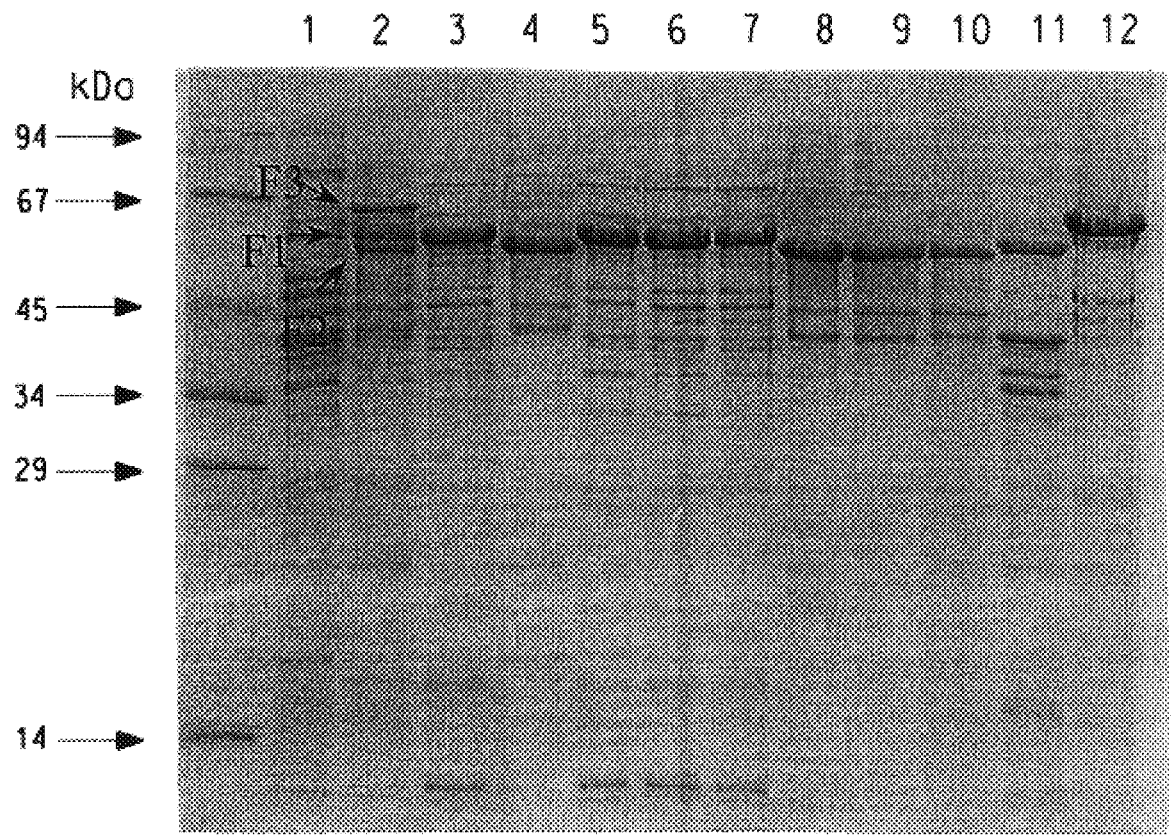
FIG. 2 shows SDS-PAGE (12.5%) with fractions after chromatography of the soluble fraction of K172 (grown anaerobically on phenol) on DEAE sepharose fast flow. See Example 4.

*Thauera aromatica* (K 172) was cultured anaerobically at 30° C. with 0.5 mM phenol and 10 mM NaHCO$_3$ as sole source of carbon and energy, as well as 2 mM NaNO$_3$ as the terminal electron acceptor. The bacterial cells were harvested and 20 g of the bacterial cells were resuspended in 20 mnL 20 mM imidazole/HCl (pH 6.5), 10% glycerol, 0.5 mM dithionite and traces of DNase I, disrupted (French Press, 137.6 MPa) and ultracentrifuged (100 000×g). The supernatant with the soluble protein firaction contained all the 4-hydroxy-benzoate:$^{14}$CO$_2$-exchange activity (383 nmol min$^{-1}$ mg$^{-1}$) and phenylphosphate carboxylase activity (10 nmol min$^{-1}$ mg$^{-1}$). The supernatant was loaded on a DEAE Sepharose fast flow chromatography column (Amersham Pharmacia Biotech, Uppsala, Sweden). FIG. 2 shows the results of SDS-PAGE (12.5%) with fractions after chromatography of the soluble fraction of K172 (grown aerobically on phenol). A total amount of 20 µg protein was loaded per lane. Lane 1: K172 grown on 4-hydroxybenzoate/NO$_3$– (10$^5$×g supernatant); Lane 2: K172 grown on phenol/NO$_3$– (10$^5$×g supernatent) show that three dominant phenol-induced proteins F1, F2, and F3 were separated. F1, F2, and F3 were identified by molecular weight: F1≈60 kDa, F2≈58 kDa, F3≈67 kDa. Lane 3: pooled fractions containing F1; Lane 4: pooled fractions containing F2; Lanes 5–7: fractions 17–19; Lanes 8–10: fractions 53–55; Lane 11: proteins that did not bind to DEAE; and Lane 12: fraction 84 containing F3.

The fraction, after chromatography on DEAE sepharose, containing F1 were pooled and loaded on a MonoQ chromatography column (Amersham Pharmacia Biotech, Uppsala, Sweden). Then the fractions containing F1 were pooled and blotted to an immobilon-P$^{sq}$ transfer membrane (Millipore, Bedford, Mass.). After staining of the PVDF membrane with Coomassie Blue, F1 was cut off and sequenced using an Applied Biosystems 473A sequencer (Table 1).

The fractions containing F2 were subjected to peptide and N-terminal sequencing. For peptide sequencing, the fractions after chromatography on DEAE sepharose containing F2 were pooled and loaded on a Blue sepharose chromatography column (Amersham Pharmacia Biotech, Uppsala, Sweden). Then the fractions containing F2 were pooled and digested with modified trypsin (Promega, Mannheim, Germany). The trypsin digest was done according to the following procedure: 500 µg protein in 200 µL of 20 mM Tris/HCl, pH 7.5, was adjusted to pH 8 with 3 µL of triethylamine. 10 µg trypsin in 10 µL H$_2$O (Promega sequencing grade modified, catalog #V5111) were added. The digest was carried out at 37° C. for 4 h. The reaction was stopped by heating for 5 min to 100° C. After centrifugation 5 µL, 70 µL and 100 µL, respectively, were applied to the HPLC. The peptides generated were separated on a reverse phase C-18 Superpac-Sephasil high performance liquid chromatography column (Amersham Pharmacia Biotech, Uppsala, Sweden). Fractions containing well resolved peptides were sequenced (Table 2).

For N-terminal sequencing, the pooled fractions after chromatography on DEAE sepharose containing F2 were loaded on a MonoQ chromatography column (Amersham Pharmacia Biotech, Uppsala, Sweden). Then the fractions containing F2 were pooled and blotted to a immobilon-P$^{sq}$ transfer membrane (Millipore, Bedford, Mass.). After staining of the PVDF membrane with Coomassie Blue, F2 was cut off and sequenced using an Applied Biosystems 473A sequencer (Table 1).

After chromatography on DEAE sepharose the pooled fractions containing F3 were loaded on a MonoQ chromatography column (Amersham Pharmacia Biotech, Uppsala, Sweden). The fractions containing F3 were pooled and blotted to a immobilon-Psq transfer membrane (Millipore, Bedford, Mass.). After staining of the PVDF membrane with Coomassie Blue, F3 was cut off and sequenced using an Applied Biosystems 473A sequencer (Table 1).

Example 5

Preparation of DNA Probe for Screening a λ EMBL3 Gene Library of *Thauera aromatica*

On the basis of the N-terminal amino acid sequences of F1, F2, and F3 and of the internal fragments of F2 (Example 4), degenerated oligonucleotides were designed. The oligonucleotides F2-forward (N-terminus) (SEQ ID NO:32; ATG-GA$^T_C$-CT$^G_C$-CG$^C_G$-TAC-TTC-ATC), F2T6-reverse (SEQ ID NO:33; TT-$^G_A$TC-$^G_A$TC-$^G_C$AG-CAT-CTG-CAT) and F2T43-reverse (SEQ ID NO:34; CAT-$^C_G$AG-GAA-$^T_C$TC-$^G_C$GC-CTG-CTG) (both internal fragments) were used as primers in a polymerase chain reaction (PCR) with genomic DNA of *Thauera aromatica* as target. PCR conditions were as follows: 100 ng target, 200 nM each primer, 200 µM each of dATP, dCTP, dTTP, dGTP, 50 mM KCl, 1.5 mM MgCl$_2$, 10 mM Tris/HCl (pH 9.0), 1 unit Taq-DNA- Polymerase (Amersham Parmacia Biotech, Uppsala, Sweden). PCR parameters were as follows: 95° C. 30 sec, 40° C. 1 min, 72° C. 2.5 min, 30 cycles. The PCR products were subjected to ethidium bromide agarose gel electrophoresis followed by excision and purification.

Figure 3:
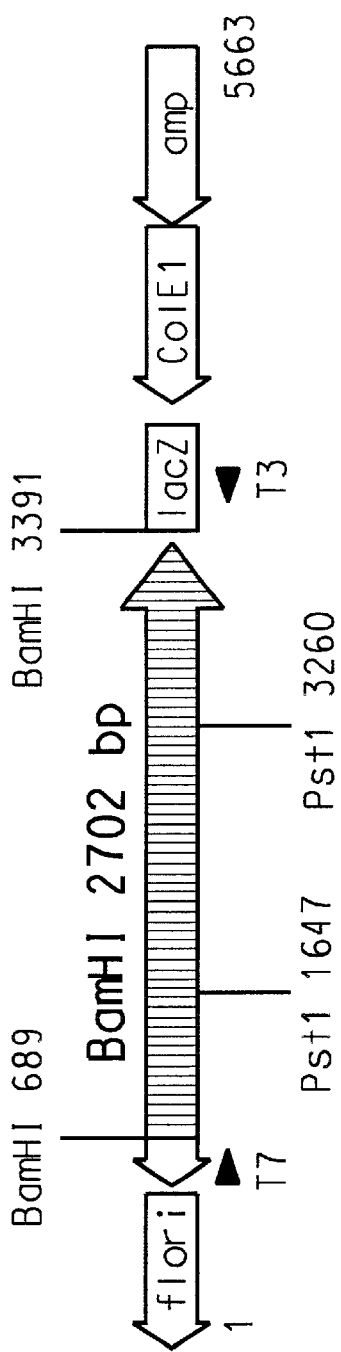
FIG. 3 shows clone 8 (pKSBam2.7). See Example 8.
Figure 4:
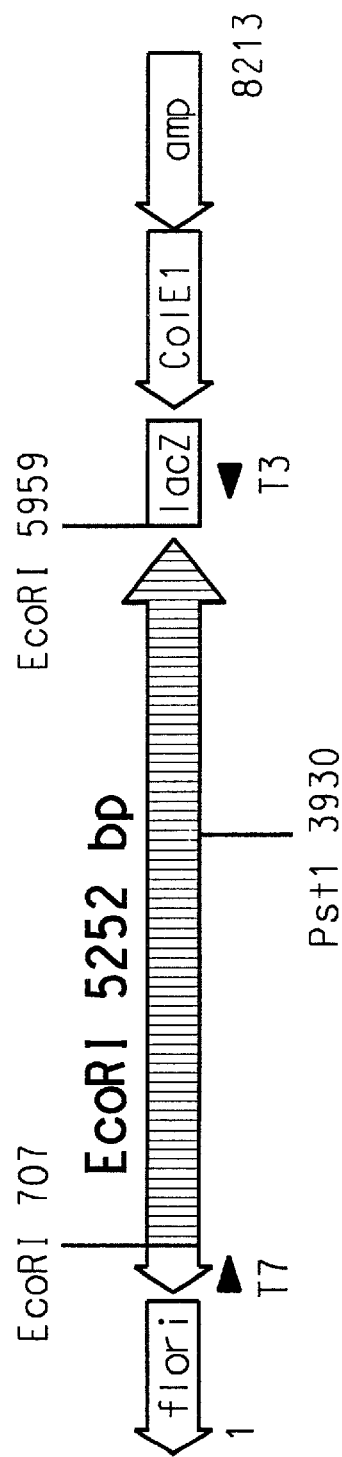
FIG. 4 shows clone 9 (pKSEco5.25). See Example 8.
Figure 5:
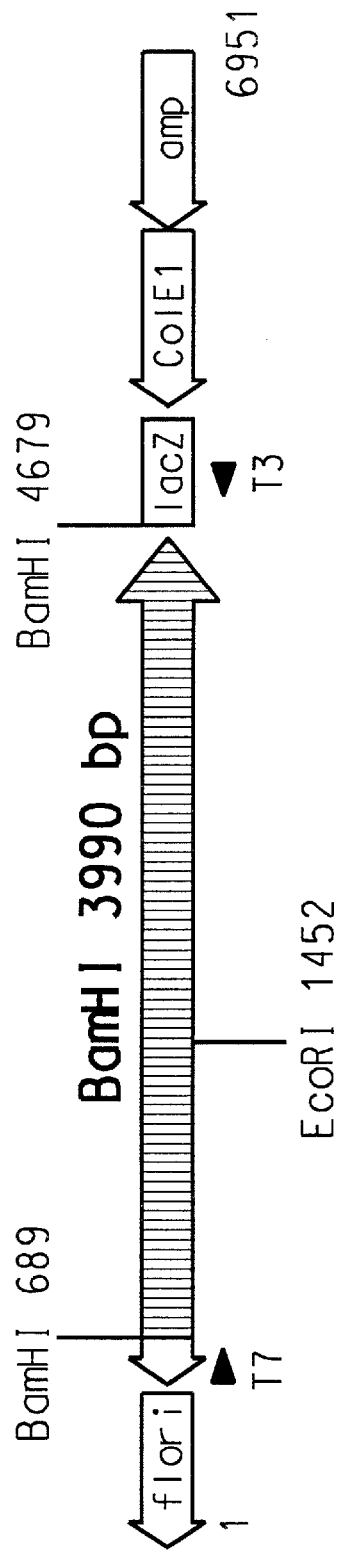
FIG. 5 shows clone 19 (pKSBam4). See Example 8.

The purified PCR product (F2-forward/F2T43 -reverse) in a size of approximately 750 bp was sequenced and confirmed to be the N-terminus of F2. The PCR product was labeled with [$^{32}$P]-dCTP and used as a probe for screening a λ EMBL3 gene library of *Thauera aromatica*. One positive phage of about 11 kb was detected, prepared and restricted with BamHI, EcoRI and Pst1. The digests were subjected to ethidium bromide agarose gel electrophoresis followed by excision and purification of the restriction fragments. The purified fragments were ligated in the corresponding pBluescript vector KS(+) [Ap$^r$, lacZ, f1, ori] restricted with BamHI, EcoRI and Pst1, respectively. Ligation mix was used to transform competent *E. coli* XL1-Blue and plated onto LB plates supplemented with IPTG, X-Gal and 50 µg/mL ampicillin. Plasmid DNA was prepared from several white colonies (clones 8, 9, and 19; FIGS. 3, 4, and 5, respectively) and sequenced by dideoxy termination protocol using T7 and T3 primer (SEQ ID NO 35: 3' CGGGATAT-CACTCAGCATAATG 5' and SEQ ID NO 36:5' AATTAAC-CCTCACTAAAGGG 3', respectively). Nucleotide sequence analysis confirmed that the amino acid sequences deduced from the genes corresponded to the N termini of F1, F2, and F3.

TABLE 1

|    | N-Terminal Amino Acid Sequence (Applied Biosystems 473A Sequencer)* | N-Terminal Amino Acid Sequence Deduced from the Genes |
|----|---|---|
| F1 | gKISA PKNNR EFIEA sVKSG DAVRI RQEVD WDNEA GAIVr RA (SEQ ID NO:24) | MGKIS APKNN REFIE ACVKS GDAVR I (SEQ ID NO:25) |
| F2 | MDLRY FINQX AEAHE LKRIT TEVDW NLEIS HVsKL XXe (SEQ ID NO:26) | MDLRY FINQC AEAHE LKRIT TEVDW NLEIS HVSKL TEE (SBQ ID NO:27) |
| F3 | MKFPV PHDIQ AKTIP GTEGw ERMYP XXXAF VXd (SEQ ID NO:28) | MKFPV PHDIQ AKTIP GTEGW ERMYP YHYQF VTD (SEQ ID NO:29) |

*The lower cases stand for amino acids that could not be clearly identified during sequencing.

TABLE 2

Internal Fragments by Trypsin-Digest: Amino Acid Sequence

F2 .FHEGG gg.
 .MQMLD DK. (SEQ ID NO:30)
 .QVADA VIASN TGSYg M.
 .FWSVV DER.
 .IXTEV DWNLE ISXV.
 .TATLW TELEQ MR.
 .YIGTM VSVVL YDPET GR.
 .GQQAE FLMAX XXXXP VXAGA EIVLE XGI. (SEQ ID NO:31)
 .GQQAE FLM..

Example 6

Figure 6:
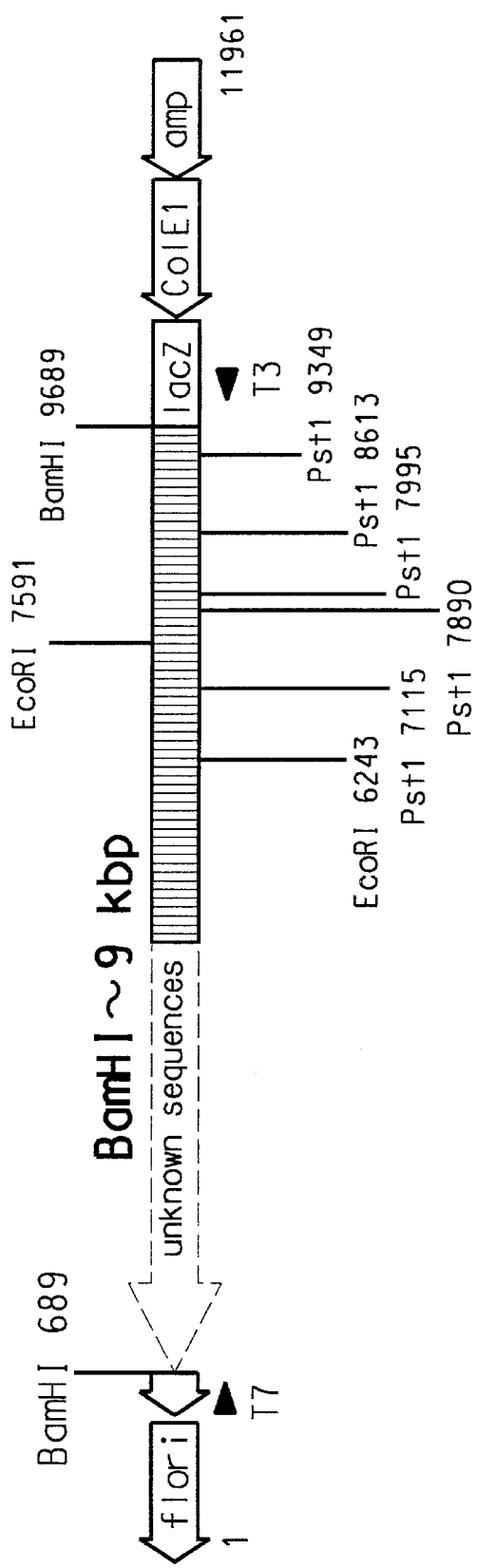
FIG. 6 shows clone 2 (pKSBam9).
Figure 7:
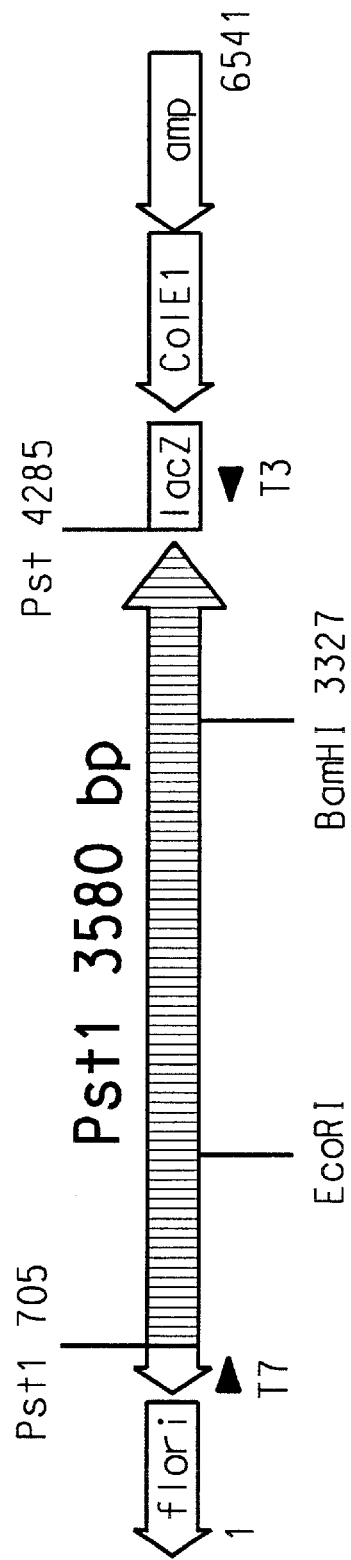
FIG. 7 shows clone 7 (pKSPst3.7). See Example 8.
Figure 12:
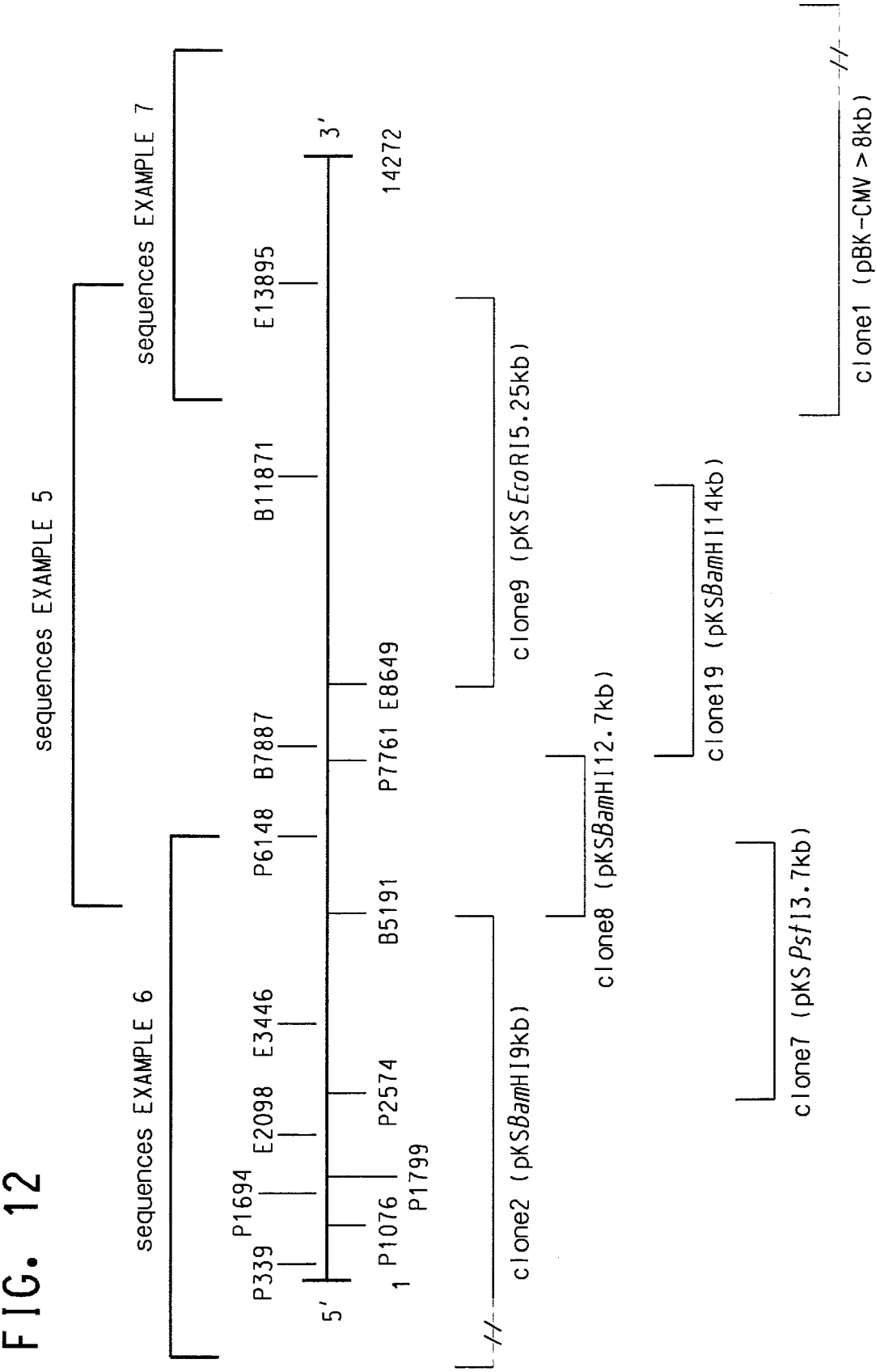
FIG. 12 shows the map of the orientation of the clones in the whole sequence of 14272 bp.

Screening of the λ EMBL3 gene library of *Thauera aromatica* for DNA Sequences 5' of the Known Sequences The oligonucleotide designated breib31(SEQ ID NO:37; 5' GACAACTTCGTCGTCAA 3') and the oligonucleotide designated breib07r3 (SEQ ID NO:38; 5' GTGGATATTG-GCTTCGGAAA 3') were used as primers in a PCR with genomic DNA of *Thauera aromatica* as target. PCR conditions were as described in Example 5. The PCR product was subjected to ethidium bromide agarose gel electrophoresis followed by excision and purification. The purified PCR product in a size of approximately 500 bp was labeled with [$^{32}$P]-dCTP and used as a probe for screening a λ EMBL3 gene library of *Thauera aromatica*. Two positive phages could be detected. The phage DNA was prepared and restricted with BamHI, EcoRI and Pst1. The digests were subjected to ethidium bromide agarose gel electrophoresis followed by excision and purification of the restriction fragments. The purified fragments were ligated in the corresponding pBluescript vector KS(+) [Ap$^r$, lacZ, f1, ori] restricted with BamHI, EcoRI and Pst1, respectively. Ligation mix was used to transform competent *E. coli* XL1-Blue which was plated onto LB plates supplemented with IPTG, X-Gal and 50 μg/mL ampicillin. Plasmid DNA was prepared from several white colonies (clone 2 with a 9 kb BamHI insert and clone 7 with a 3.7 kb Pst1 insert as described in FIGS. 6 and 7) and sequenced by dideoxy termination protocol using T3 primer (SEQ ID NO:36). DNA sequences upstream of the known sequences were revealed by DNA analysis (FIG. 12).

Example 7

Figure 8:
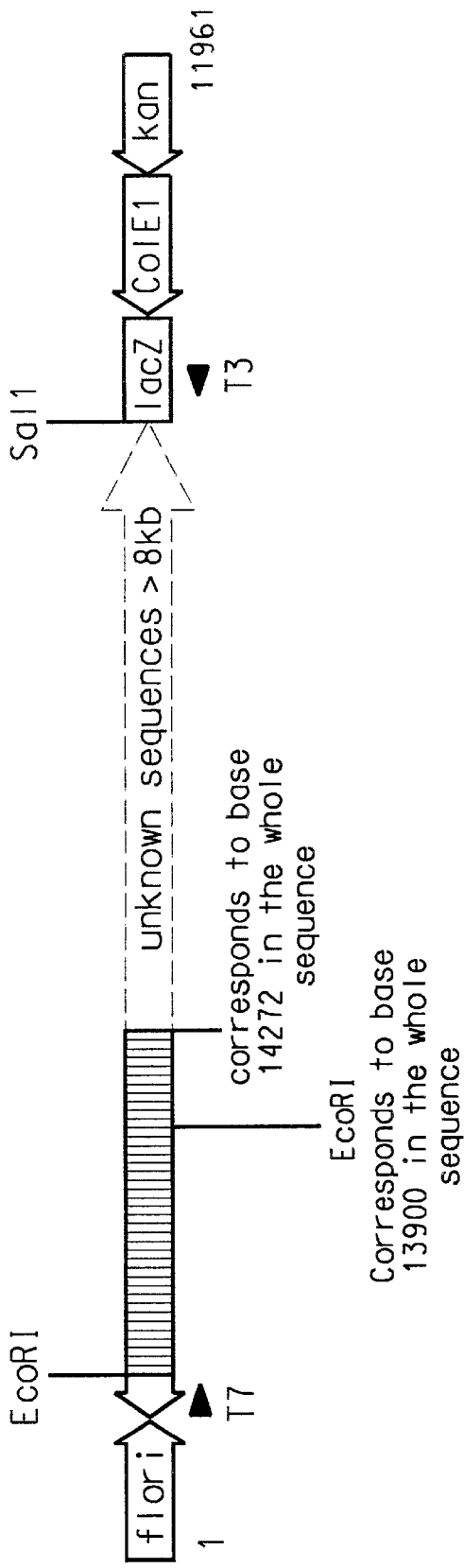
FIG. 8 shows phagemid-vector—clone 1 (pBK-CMV).

Screening of the λ zap Express Gene Library of *Thauera aromatica* for DNA Sequences 3' of the Known Sequences The oligonucleotide designated λ15-forward (SEQ ID NO:39; 5' TCGCCGGCGACGACGCCG 3') and the oligonucleotide designated λ15-reverse (SEQ ID NO:40; 5' CCGCGCGCTGCGCCGCCG 3') were used as primers in a PCR with genormic DNA of *Thauera aromatica* as target. PCR conditions were as follows: 100 ng target, 200 nM each primer, 200 μM each of dATP, dCTP, dTTP, dGTP, (NH$_4$)SO$_4$, KCl, 4.5 mM MgCl$_2$, 10 mM Tris/HCl (pH 8.7), 1× Q solution, 1 unit Taq-DNA-Polymerase (Qiagen, Hilden, Germany). PCR parameters were as follows: 95° C. 30 sec, 45° C. 1 min, 72° C. 2.5 min, 30 cycles. The PCR product was subjected to ethidium bromide agarose gel electrophoresis followed by excision and purification. The purified PCR product in a size of approximately 600 bp was labeled with [$^{32}$P]-dCTP and used as a probe for screening a λ zap express gene library (Stratagene, Heidelberg, Germany) of *Thauera aromatica*. One positive clone was detected. The phagemid was prepared according to the manufacturer's protocol and restricted with Sal1/EcoRI. After ethidium bromide agarose gel electrophoresis of the digest, the DNA insert was estimated to be 9 kb in size (clone 1—FIG. 8). The restricted DNA was blotted and hybridized with [$^{32}$P]-labeled probe designated as described above. A fragment of approximately 1 kb could be detected. DNA sequences downstream of the known sequences were revealed by DNA analysis (FIG. 12).

Example 8

DNA Sequencing of the Genes Coding for Putative Proteins Involved in Phenol Metabolism A 3.7-kb Pst1 fragment, a 2.7-kb BamHI fragment, a 4.0-kb BamHI fragment, a 5.25-kb EcoRI fragment and a 9 kb BamHI fragment were each ligated to the corresponding pBluescript KS(+) [Ap$^r$, lacZ, f1, ori] vector restricted with BamHI, Pst1 and EcoRI, respectively (FIGS. 7, 3, 5, and 4, respectively). The plasmids were transformed into competent *E. coli* XL1-blue. Plasmid DNA purified by alkaline lysis method was sequenced by dideoxy termination protocol using T7 and T3 primers (SEQ ID NO:35 and SEQ ID NO:36, respectively) and then by primer walking. About 14 kb (SEQ ID NO:23) were sequenced which contained two gene clusters that appear to be involved in phenol metabolism.

Figure 13:
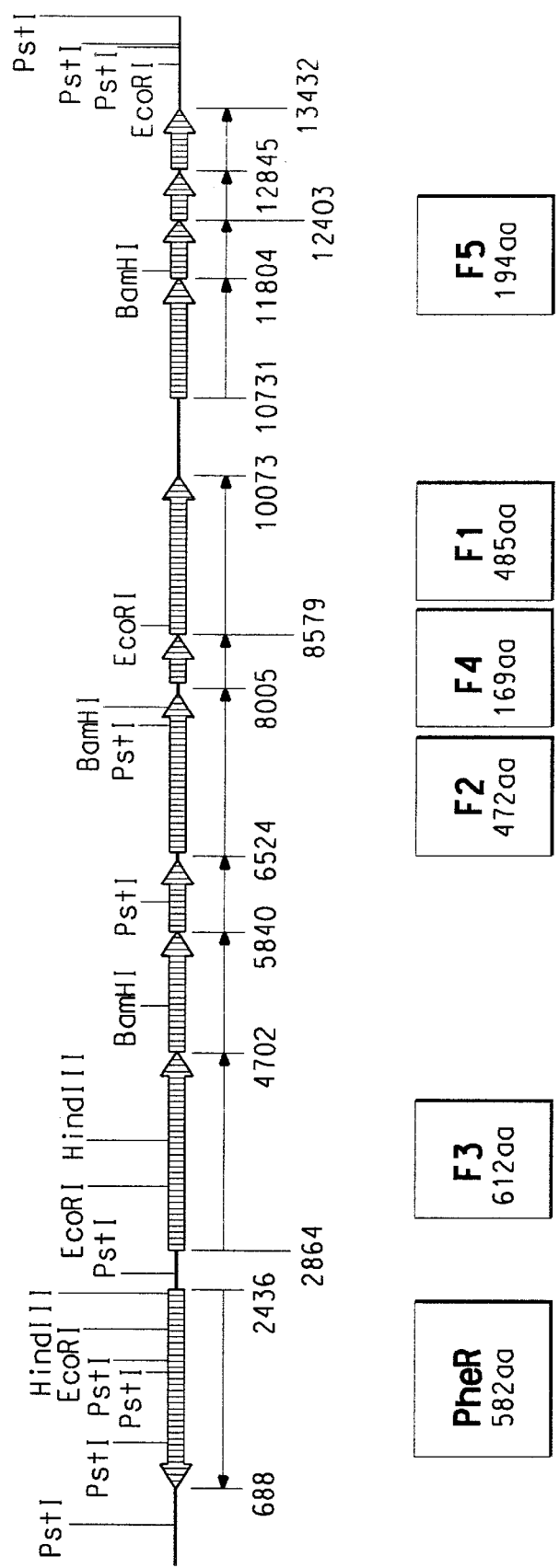
FIG. 13 shows the organization of the genes, with restriction sites, involved in phenol metabolism of *Thauera aromatica*.

The nucleotide sequences of F1, F2, and F3 are provided in SEQ ID NO:2, SEQ ID NO:4, and SEQ ID NO:6, respectively, and their deduced amino acid sequences are provided in SEQ ID NO:1, SEQ ID NO:3, and SEQ ID NO:5, respectively. Nucleotide and amino acid sequences were analyzed using the PC/gene software package (Genofit). Homologous sequences were identified using the BLAST (Basic Local Alignment Search Tool; Altschul et al., *J. Mol. Biol.* 215:403–410 (1990)) search using the TBLASTN algorithm provided by the National Center for Biotechnology Information (Table 4 and FIG. 13).

Figure 11:
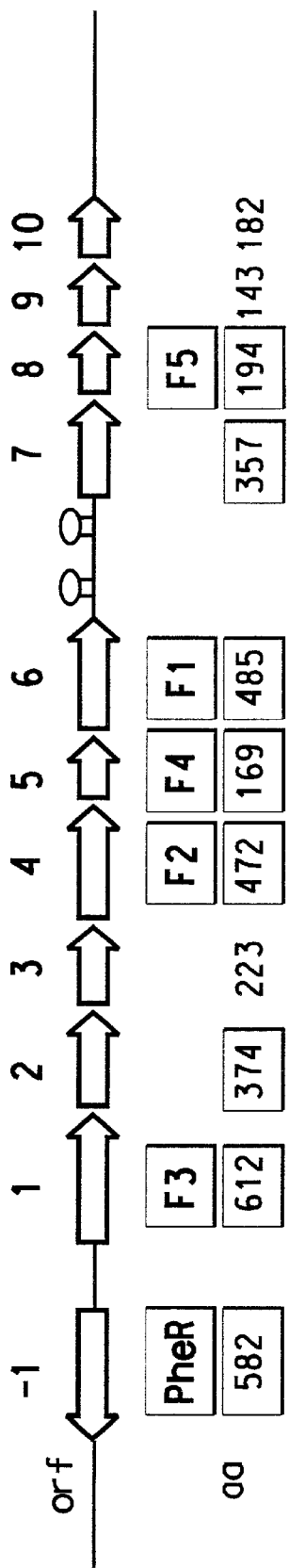
FIG. 11 shows the organization of the genes possibly involved in anaerobic phenol metabolism of *Thauera aromatica* and their homologies to known proteins.
Figure 11:
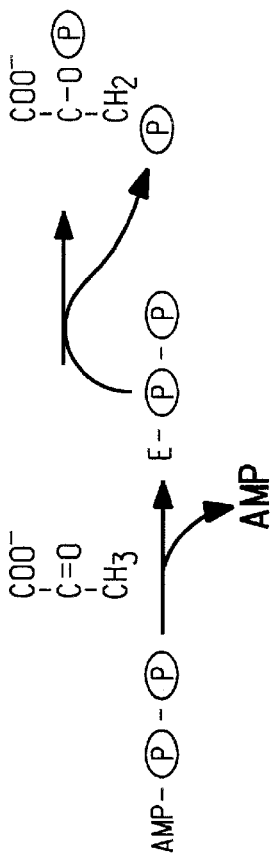
Figure 11:
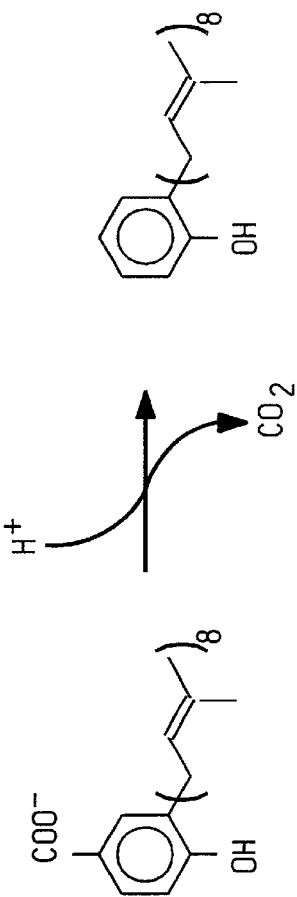

F3 shows homology to phosphoenolpyruvate (PEP) synthase. The reaction catalyzed by this enzyme is shown in FIG. 11. First, PEP-synthase is phosphorylted by ATP, AMP and Pi being the products. In a second step, the phosphorylated enzyme transfers the 0-phosphoryl group of ATP to pyruvate. This reaction may be similar to the proposed reaction mechanism of the phenol kinase, whereby phenol ultimately becomes phosphorylated.

F1, F2, and F5 show good homology to the ubiD, a gene which codes for the 3-octaprenyl-4-hydroxybenzoate decarboxylase. This enzyme is involved in the biosynthesis of ubiquinone. The reaction catalyzed is shown in FIG. 11. This reaction is analogous to the reverse reaction of the postulated carboxylation of phenol.

Example 9

Expression of F1–F5 Proteins in *E. coli*

A 3.7-kb Pst1 fragment contains: orf1 (SEQ ID NO:6) which codes for F3 protein (SEQ ID NO:5) and orf2 (SEQ ID NO:12) which codes for unknown protein (SEQ ID NO:11). A 2.7-kb BamHI fragment contains: orf3 (SEQ ID NO:14) which codes for unknown protein (SEQ ID NO:13) and orf4 (SEQ ID NO:4) which codes for F2 protein (SEQ ID NO:3). A 4.0-kb BamHI fragment contains: orf5 (SEQ ID NO:8) which codes for F4 protein (SEQ ID NO:7), orf6 (SEQ ID NO:2) which codes for F1 protein (SEQ ID NO:1), and orp7 (SEQ ID NO:16) which codes for unknown protein (SEQ ID NO:15). A 5.25-kb EcoRI fragment contains: orp7 (SEQ ID NO:16) which codes for unknown protein, SEQ ID NO:15), orf8 (SEQ ID NO:10) which codes for F5 protein (SEQ ID NO:9), or)9 (SEQ ID NO:18) which codes for unknown protein, SEQ ID NO:17), and orf10 (SEQ ID NO:20) which codes for unknown protein, SEQ ID NO:19). Each restriction fragment was ligated into pBluescript SK.

Figure 9:
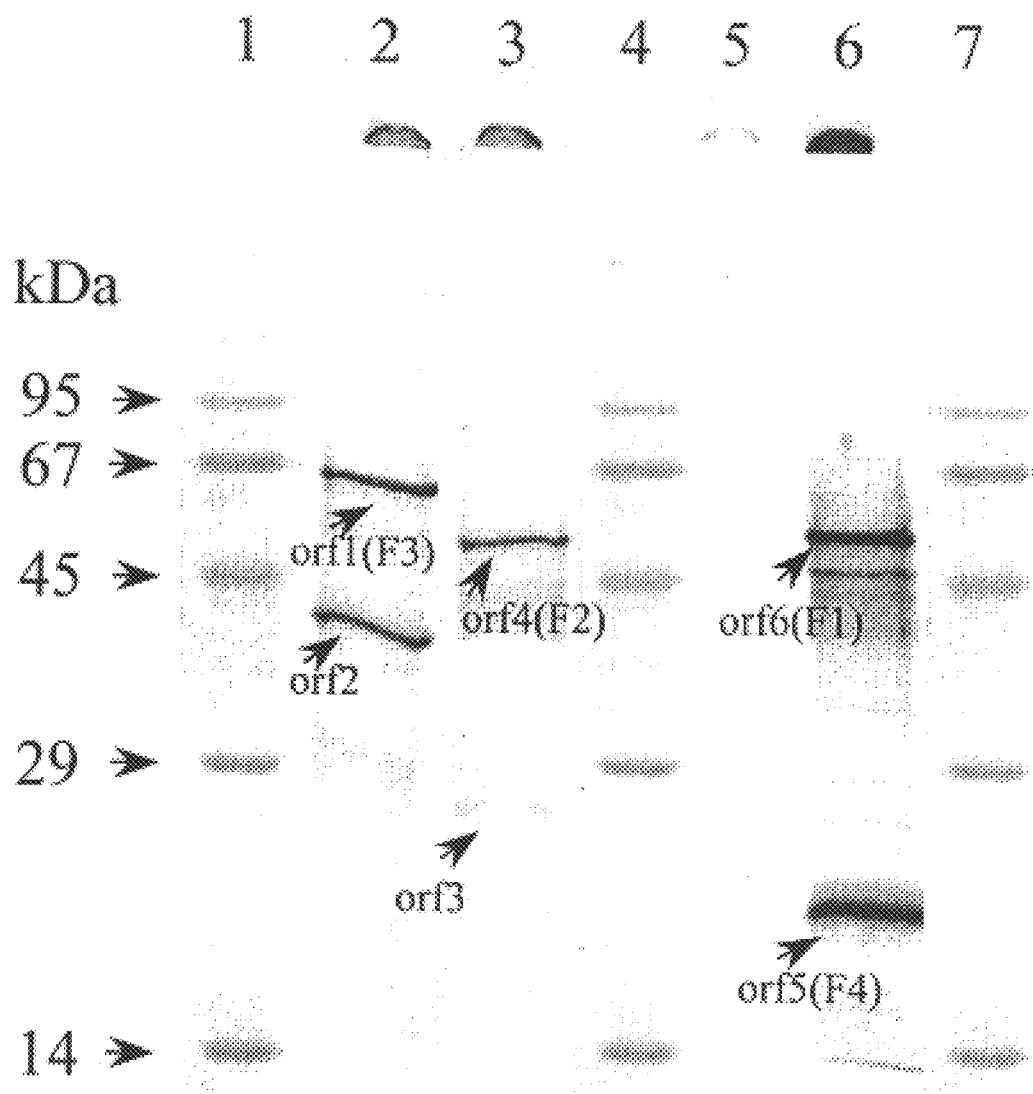
FIG. 9 shows the expression of F1–F5 in *E. coli*. See Example 9.

For expression of the genes, the recombinant plasmids were transformed into *E. coli* K38 containing the plasmid pGP 1–2 [kan$^r$, cI857 T7Gen1(RNA Polymerase)] (Tabor and Richardson, 1985). Cells were grown in 1 mL Luria-Bertani medium plus ampicillin and kanamycin at 30° C. to an absorbance of 0.5 at 600 nm, washed in Werkman miinimal medium (Fraenkel and Neidhardt, 1961) and resuspended in 5 mL Werkman minimal medium containing 0.01% (mass/volume) amino acids besides cysteine and methionine. After incubation for 1–2 h at 30° C. the temperature was shifted to 42° C. to induce expression of T7 polymerase. After 15 min *E. coli* RNA synthesis was stopped by addition of 200 μg rifampicin/mL. The cells were incubated for 10 min at 42° C. and for further 20 min at 30° C. to ensure degradation of *E. coli* mRNA. Aliquots of 1 mL of the induced culture were subsequently pulse-labeled with 10 μCi [$^{35}$S]methionine (Amersham) for 5 min at 30° C. Cells were centrifuged, resuspended in 120 μL sample buffer and lysed by 5 min incubation at 95° C. Labeled proteins were separated by sodium dodecyl sulfate gel electrophoresis and localized by autoradiography. FIG. 9 shows the experimentally determined molecular masses of the proteins. Expression of F1–F5 in *E. coli* (T7 experiment). 25 μL were loaded on each lane. Lanes 1, 4, 7: marker proteins; Lane 2: Proteins (F3 & unknown) coded by 3.7 kb Pst1 fragment containing orf and ory2 respectively; Lane 3: Proteins (unknown & F2) coded by 2.7 kb BamHI fragment containing orf3 and orf4 respectively; Lane 5: Proteins (F5 and 3 unknowns) coded by 5.25 kb EcoRI fragment containing orf8, orf7, orf9 and orf10 respectively; and Lane 6: Proteins (F1, F4 and unknown) coded by 4.0 kb BamHI fragment containing orf6, orf5 and orf7. The predicted molecular masses agreed reasonably well with the experimentally determined molecular masses of FIG. 9.

Example 10

Figures 10A, 10B:
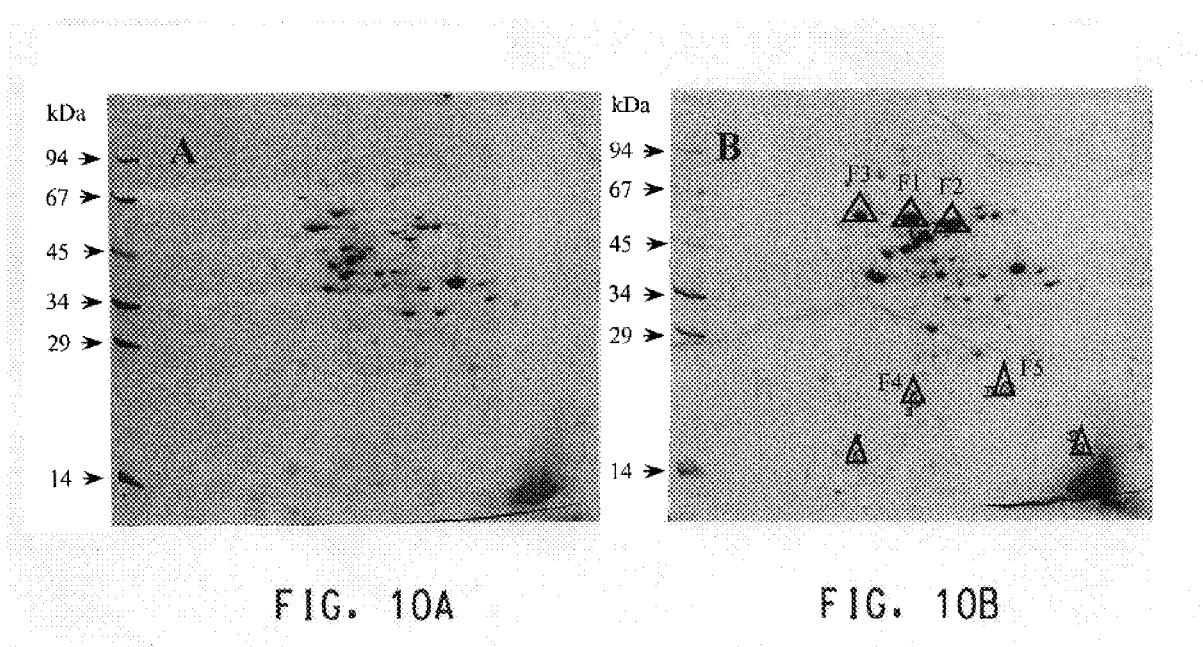
FIGS. 10A and 10B show the two dimensional gel electrophoresis of 100 000×g supernatant of *Thauera aromatica* anaerobically grown on 4-hydroxybenzoate (A) and phenol (B), respectively. Phenol-induced proteins are indicated by triangulars.

Extraction and N-terminal Sequencing of Phenol-induced Proteins F4 and F5 Using Two Dimensional Gel Electrophoresis 120 μg of the soluble fraction of cells that were grown on phenol/nitrate and of cells grown on 4-hydroxybenzoate, respectively, were lysed in 10 μL lysis buffer (9.5 M urea, 2% (w/v) CHAPS, 0.8% (w/v) ampholytes pH 3–10 (40% (w/v); Biorad), 1% (w/v) DTT, traces of bromophenol blue) and applied to a rehydrated Immobiline Dry Strip (linear pH gradient 3–10; Pharmacia) according to the manufacturers protocol (rehydration buffer: 8 M urea, 0.5% (w/v) CHAPS, 15 mM DTT, 0.2% (w/v) ampholytes pH 3–10 (40% (w/v); Biorad). The horizontal isoelectric focussing was run overnight (15 h, 1400 V). After the first dimension the Immobiline Dry Strips were equilibrated twice for 15 min in equilibration buffer (0.05 M Tris/HCl pH 8.8, 6 M urea, 30% (w/v) glycerol, 2% (w/v) SDS, traces of bromophenol blue and 10 mg/nL DTT or 48 mg/mL iodoacetamide, respectively). The second dimension was a vertical SDS polyacrylamide gel electrophoresis (11.5% polyacrylamide) indicating phenol-induced proteins (FIG. 10). The proteins were blotted to a PVDF membrane and stained with Coomassie Blue. The phenol-induced proteins F4 and F5 were cut off and N-terminal sequenced using an Applied Biosystems 473A sequencer (Table 3). Analysis of the amino acid sequence and translation into nucleotide sequence confirmed the genes encoding for F4 and F5. Furthermore, the predicted molecular masses agreed reasonably well with the experimentally determined masses.

TABLE 3

| N-Terminal Amino Acid Sequence (Applied Biosystems 473A Sequencer) | N-Terminal Amino Acid Sequence Deduced from the Genes |
| --- | --- |
| F4 MEQAK NIKLV (SEQ ID NO:41) | MEQAK NIKLV (SEQ ID NO:42) |
| F5 MRIVV GMXGA (SEQ ID NO:43) | MRIVV GMSGA (SEQ ID NO:44) |

Example 11

Identification of Genes Coding for Phenol-Induced Proteins

About 14 kb of the λ EMBL3 gene library were sequenced (SEQ ID NO:23). The nucleotide sequence was analyzed with The ORF Finder (Open Reading Frame Finder) (http://www.ncbi.nlm.nih.gov/gorf/gorf.html) to find the open reading frames (ORFs). Eleven ORFs could be detected (orfs1–10 and orf-1) as shown in FIG. 11.

Analysis of the sequence revealed 10 ORFs that were transcribed in the same direction. The first six ORFs were separated by less than 65 bp and totaled 7210 bp. This cluster of putative genes was followed by a 658 bp non-coding region containing putative secondary structures.

Another cluster of putative genes followed which also showed less than 40 bp intergenic regions. Downnrream of orf10 470 bp were sequenced; however this appeared not to code for proteins. Upstream of orf1 and transcribed in the opposite direction another putative gene was found which was separated by 428 bp from orf1.

The nucleotide sequence of an ORF is automatically transcribed in amino acid sequence by the ORF Finder. Comparison of deduced amino acid sequences of orf1–10 and orf-1 (see FIG. 11) with the experimentally determined N-terminal amino acid sequences of phenol-induced proteins and the internal sequences revealed that the following ORFs coded for known proteins. orf1 (SEQ ID NO:6) for F3, orf4 (SEQ ID NO:4) for F2, orf5 (SEQ ID NO:8) for F4, orf6 (SEQ ID NO:2) for F1 and orf8 (SEQ ID NO:10) for F5. The predicted molecular masses agreed reasonably well with the experimentally determined masses (FIG. 10).

The deduced amino acid sequences of the ORFs was analyzed by using the BLAST search (Basic Local Alignment Search Tool; Altschul et al., *J. Mol. Biol.* 215:403–410 (1990)) using the BLASTP 2.0.8 algorithm (http://www.ncbi.nlm.nih.gov/cgi-bin/BLAST/nph-newblast) provided by the National Center for Biotechnology Information and by using the BLAST+BEAUTY searches using the NCBI BLAST Server (http://dot.imgen.bcm.tmc.edu:9331/seq-search/Options/beauty_pp.html) (Tables 4 and 5). Table 4 contains homologous hits and Table 5 contains hits with the highest homology.

orf1 (SEQ ID NO:6) and orf2 (SEQ ID NO:12) are likely to encode for the phenol-phosphorylating enzyme $E_1$. This conclusion is deduced from the high similarity of the genes with the domains of PEP synthase of *E. coli*. PEP synthase catalyzes a similar posphorylation reaction (FIGS. 1 and 11).

orf4 (SEQ ID NO:4), orf6 (SEQ ID NO:2), orfi (SEQ ID NO:16) and orf8 (SEQ ID NO:10) are likely to represent the carboxylating enzyme $E_2$. This conclusion is deduced from the high similarity of the genes with two enzymes of *E. coli* that catalyze the decarboxylation of a 4-hydroxybenzoate isoprene derivative to the corresponding phenolic product (ubiD and ubiX). This reaction is formally equal to the phenol carboxylation reaction (FIGS. 1 and 11).

The function of the proteins encoded by orf3 (SEQ ID NO:14), orf5 (SEQ ID NO:8), orf9 (SEQ ID NO:18) and orf10 (SEQ ID NO:20) are unknown, and have low homology to other known sequences.

TABLE 4

| ORF | Similarity Identified | SEQ ID Nucleotide | SEQ ID Amino Acid | % Identity[a] | % Similarity[b] | E-value[c] |
|---|---|---|---|---|---|---|
| −1 582 aa | gnl\|PID\|d1010531 (D63814) pheR [*Pseudomonas putida*] 563 aa | 22 | 21 | 47.2 | 72.3 | 1e-20 |
| 1 612 aa | gi\|147146(M69116) PEP synthase [*E. coli*] 793 aa | 6 | 5 | 16.7 | 39.3 | 4e-10 |
| 2 233 aa | gi\|147146(M69116) PEP synthase [*E. coli*] 793 aa | 12 | 11 | 21.8 | 34.5 | 1e-63 |
| 3 223 aa | gi\|2621183(AE000803) inosine-5'-monophosphate dehydrogenase [*Methanobacterium thermoautotrophicum*] 484 aa | 14 | 13 | 14.5 | 30.2 | 1e-8 |
| 4 472 aa | gi\|549586\|sp\|P26615\| yigC [*E. coli*] 497 aa | 4 | 3 | 30.8 | 58.95 | 5e-47 |
| 5 169aa | gi\|2851406\|sp\|P45396\| yrbI [*E. coli*] 188 aa | 8 | 7 | 38.8 | 63.8 | 2e-25 |
| 6 485 aa | gi\|549586\|sp\|P26615\| yigC [*E. coli*] 497 aa | 2 | 1 | 29.4 | 57.1 | 1e-31 |
| 7 357aa | gi\|549586\|sp\|P26615\| yigC [*E. coli*] 497 aa | 16 | 15 | 24.7 | 47.5 | 7e-25 |
| 8 194 aa | gi\|2507150\|sp\|P09550\| ubiX [*E. coli*] 189 aa | 10 | 9 | 60.3 | 86.8 | 5e-56 |
| 9 143 aa | gi\|2622617(AE000910) conserved protein [*Methanbacterium thermo.*] 122 aa | 18 | 17 | 40 | 64.8 | 8e-13 |
| 10 182 aa | gi\|2129134\|pir\|D64443\| mutator protein mutT [*Methanoccus jann.*] 169 aa | 20 | 19 | 36.1 | 62.7 | 2e-9 |

[a]%Identity is defined as percentage of amino acids that are identical between the two proteins.
[b]%Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.
aa: amino acids
Citation: BCM Search Launcher - Pairwise Sequence Alignment
ALIGN - optimal global alignment with no short-cuts (EERIE) - (http://dot.imgen.bcm.tmc.edu:9331/seq-search/alignment.html)

TABLE 5

| Name | Gene | Dir | Range | | Amino Acid Size | Top Hit |
|---|---|---|---|---|---|---|
| PheR | Transcriptional regulator | ← | 688 | 2479 | 582 | gi\|3445531 (AF026065) positive phenol-degradative gene regulator |
| F3 | PEP Synthase | → | 2864 | 4703 | 612 | sp\|O29548\|PPSA_ARCFU PROBABLE PHOSPHOENOLPYRUVATE SYNTHASE |
|  | PEP Synthase | → | 4707 | 5841 | 374 | sp\|P46893\|PPSA_STAMA PROBABLE PHOSPHOENOLPYRUVATE SYNTHASE (PYRUVATE, WATER DIKINASE) (PEP SYNTHASE) |
|  | inosine-5'-monophosphate dehydrogenase | → | 5853 | 6525 | 223 | gi\|2621183 (AE000803) inosine-5'-monophosphate dehydrogenase [*Methanobacterium thermoautotrophicum*] |
| F2 | hypothetical protein (oxidoreductase) | → | 6587 | 8006 | 472 | gi\|2650432 (AE001091) conserved hypothetical protein [*Archaeoglobus fulgidus*] |
| F4 | YRBI_ECOLI HYPOTHETICAL | → | 8070 | 8580 | 169 | sp\|P45396\|YRBI_ECOLI HYPOTHETICAL 20.0 KD PROTEIN IN MURA-RPON INTERGENIC REGION |

TABLE 5-continued

| Name | Gene | Dir | Range | | Amino Acid Size | Top Hit |
|---|---|---|---|---|---|---|
| F1 | probable membrane protein | → | 8589 | 10074 | 485 | pirIIS62018 probable membrane protein YDR539w - yeast (*Saccharomyces cerevisiae*) |
| | Conserved Hypothetical (oxidoreductase?) | → | 10773 | 11805 | 357 | gi|2622505 (AE000902) conserved protein [*Methanobacterium thermoautotrophicum*] |
| F5 | Decarboxylase | → | 11819 | 12404 | 194 | sp|PO9550|UBIX-ECOLI 3-OCTAPRENYL-4-HYDROXYBENZOATE CARBOXY-LYASE (POLYPRENYL P-HYDROXYBENZOATE DECARBOXYLASE) |
| | conserved protein | → | 12414 | 12846 | 143 | gi|2622617 (AE000910) conserved protein [*Methanobacterium thermoautotrophicum*] |
| | mutator MutT protein | → | 12884 | 13433 | 182 | gi|2622420 (AE000895) mutator MutT protein [*Methanobacterium thermoautotrophicum*] |

We claim:

1. An isolated and purified DNA fragment as set forth in SEQ ID NO:23.

2. A microorganism stably transformed with a chimeric gene having at least one copy of the nucleic acid sequence of SEQ ID NO:23.

* * * * *

SEQUENCE LISTING

```
<160> NUMBER OF SEQ ID NOS: 44

<210> SEQ ID NO 1
<211> LENGTH: 485
<212> TYPE: PRT
<213> ORGANISM: Thauera aromatica

<400> SEQUENCE: 1
```

Met Gly Lys Ile Ser Ala Pro Lys Asn Asn Arg Glu Phe Ile Glu Ala
 1               5                  10                  15

Cys Val Lys Ser Gly Asp Ala Val Arg Ile Arg Gln Glu Val Asp Trp
                20                  25                  30

Asp Asn Glu Ala Gly Ala Ile Val Arg Arg Ala Cys Glu Leu Ala Glu
            35                  40                  45

Ala Ala Pro Phe Met Glu Asn Ile Lys Asp Tyr Pro Gly Phe Ser Tyr
        50                  55                  60

Phe Gly Ala Pro Leu Ser Thr Tyr Arg Arg Met Ala Ile Ser Leu Gly
 65                  70                  75                  80

Met Asp Pro Ala Ser Thr Leu Pro Gln Ile Gly Ala Glu Tyr Leu Lys
                85                  90                  95

Arg Thr Asn Ser Glu Pro Val Ala Pro Val Ile Val Asp Lys Arg Asp
            100                 105                 110

Ala Pro Cys Lys Glu Asn Ile Leu Leu Gly Ala Asp Val Asp Leu Thr
        115                 120                 125

Lys Leu Pro Val Pro Leu Val His Asp Gly Asp Gly Arg Tyr Val
    130                 135                 140

Gly Thr Trp His Ala Val Ile Thr Lys His Pro Val Arg Gly Asp Val
145                 150                 155                 160

Asn Trp Gly Met Tyr Arg Gln Met Met Trp Asp Gly Arg Thr Met Ser
                165                 170                 175

Gly Ala Val Phe Pro Phe Ser Asp Leu Gly Lys Ala Leu Thr Glu Tyr
            180                 185                 190

Tyr Leu Pro Arg Gly Glu Gly Cys Pro Phe Ala Thr Ala Ile Gly Leu
        195                 200                 205

Ser Pro Leu Ala Ala Met Ala Ala Cys Ala Pro Ser Pro Ile Pro Glu
    210                 215                 220

Pro Glu Leu Thr Gly Met Leu Ala Gly Glu Pro Val Arg Leu Val Lys
225                 230                 235                 240

Cys Glu Thr Asn Asp Leu Glu Val Pro Ala Asp Ala Glu Ile Ile Ile

|     |     |     |     |     | 245 |     |     |     | 250 |     |     |     |     | 255 |     |
| --- | --- | --- | --- | --- | --- | --- | --- | --- | --- | --- | --- | --- | --- | --- | --- |
| Glu | Gly | Val | Ile | Leu | Pro | Asp | Tyr | Lys | Val | Glu | Gly | Pro | Phe | Gly |     |
|     |     |     |     | 260 |     |     |     |     | 265 |     |     |     | 270 |     |     |

Glu Tyr Thr Gly Tyr Arg Thr Ser Pro Arg Asp Phe Arg Val Thr Phe
         275                 280                 285

Arg Val Asp Ala Ile Thr Tyr Arg Asn Asn Ala Thr Met Thr Ile Ser
     290                 295                 300

Asn Met Gly Val Pro Gln Asp Glu Gly Gln Leu Leu Arg Ser Phe Ser
305                 310                 315                 320

Leu Gly Leu Glu Leu Glu Lys Leu Leu Lys Ser Gln Gly Ile Pro Val
                 325                 330                 335

Thr Gly Val Tyr Met His Pro Arg Ser Thr His His Met Met Ile Val
             340                 345                 350

Gly Val Lys Pro Thr Tyr Ala Gly Ile Ala Met Gln Ile Ala Gln Leu
             355                 360                 365

Ala Phe Gly Ser Lys Leu Gly Pro Trp Phe His Met Val Met Val Val
370                 375                 380

Asp Asp Gln Thr Asp Ile Phe Asn Trp Asp Glu Val Tyr His Ala Phe
385                 390                 395                 400

Cys Thr Arg Cys Asn Pro Glu Arg Gly Ile His Val Phe Lys Asn Thr
                 405                 410                 415

Thr Gly Thr Ala Leu Tyr Pro His Ala Thr Pro His Asp Arg Lys Tyr
             420                 425                 430

Ser Ile Gly Ser Gln Val Leu Phe Asp Cys Leu Trp Pro Val Asp Trp
             435                 440                 445

Asp Lys Thr Asn Asp Val Pro Thr Leu Val Ser Phe Lys Asn Val Tyr
         450                 455                 460

Pro Lys Asp Ile Gln Glu Lys Val Thr Asn Asn Trp Thr Asp Tyr Gly
465                 470                 475                 480

Phe Lys Pro Val Lys
                485

<210> SEQ ID NO 2
<211> LENGTH: 1458
<212> TYPE: DNA
<213> ORGANISM: Thauera aromatica

<400> SEQUENCE: 2

```
atgggaaaga tttcagcacc gaaaaacaac cgtgaattca tcgaggcatg cgtcaagtcc      60
ggcgatgcgg tccggatcag acaggaagtg gactgggaca cgaggccgg cgccatcgtg     120
cgccgcgcct gcgagctcgc cgaagccgcc ccgttcatgg agaacatcaa ggactacccc     180
ggcttcagct acttcggcgc gccgctgtcg acctaccgcc gcatggcgat ctcgctcggc     240
atggacccgg catcgacctt gccgcagatc ggcgccgagt acctcaaacg taccaacagc     300
gagcccgtgg cgccggtgat cgtcgacaaa cgggacgccc cgtgcaagga gaacatcctg     360
ctcggcgccg acgtcgatct gaccaagctg ccggtaccgc tggtccatga cggcgacggc     420
ggccgctacg tcggcacctg cacgcggtg atcaccaagc accggtgcg cggcgacgtg     480
aactggggca tgtaccggca gatgatgtgg gacggccgca cgatgtcggg cgccgtgttc     540
ccgttctcgg atctgggcaa ggcgctcacc gagtactacc tgccgcgcgg cgagggctgc     600
ccgttcgcga ccgcgatcgg cctgtcgccg ctcgccgcga tggccgcctg cgcgccctct     660
ccgatccccg agcccgagct caccggcatg ctcgccggca gccggtgcg cctggtgaag     720
```

-continued

```
tgcgagacca acgacctcga agtcccggcc gatgccgaga tcatcatcga gggcgtgatc      780
ctgcccgact acaaggtcga ggaaggcccg ttcggcgaat acaccggcta ccgcaccagc      840
ccgcgcgact tccgcgtcac cttccgcgtc gatgcgatca cctatcgcaa caacgcgacg      900
atgacgatct cgaacatggg cgtgccgcag gacgagggcc agctgctgcg ctcgttctcg      960
ctcgggctcg aactcgagaa gctgctgaag agccagggta tcccggtgac cggcgtgtac     1020
atgcacccgc gctcgaccca ccacatgatg atcgtcggcg tgaagccgac ctacgccggc     1080
atcgcgatgc agatcgcgca gctcgcgttc ggctccaagc tcgggccgtg gttccacatg     1140
gtgatggtgg tcgacgacca gaccgacatc ttcaactggg acgaggtcta tcacgcgttc     1200
tgcacgcgct gcaatccgga gcgcggcatc cacgtgttca agaacaccac cggcaccgcc     1260
ctctatccgc acgccacccc gcacgaccgc aagtactcga tcggctcgca ggtgctgttc     1320
gattgcctgt ggccggtcga ttgggacaag accaacgacg tgccgacgct cgtcagcttc     1380
aagaacgtct atccgaagga catccaggaa aaggtcacga caactggac cgactacggc      1440 ttcaagccgg tgaaataa                                                  1458
```

<210> SEQ ID NO 3
<211> LENGTH: 472
<212> TYPE: PRT
<213> ORGANISM: Thauera aromatica

<400> SEQUENCE: 3

```
Met Asp Leu Arg Tyr Phe Ile Asn Gln Cys Ala Glu Ala His Glu Leu
 1               5                  10                  15

Lys Arg Ile Thr Thr Glu Val Asp Trp Asn Leu Glu Ile Ser His Val
            20                  25                  30

Ser Lys Leu Thr Glu Glu Lys Lys Gly Pro Ala Leu Leu Phe Glu Ser
        35                  40                  45

Ile Lys Gly Tyr Asp Thr Pro Val Phe Thr Gly Ala Phe Ala Thr Thr
    50                  55                  60

Lys Arg Leu Ala Val Met Leu Gly Leu Pro His Asn Leu Ser Leu Cys
65                  70                  75                  80

Glu Ser Ala Gln Gln Trp Met Lys Lys Thr Ile Thr Ser Glu Gly Leu
                85                  90                  95

Ile Lys Ala Lys Glu Val Lys Asp Gly Pro Val Leu Glu Asn Val Leu
            100                 105                 110

Ser Gly Asp Lys Val Asp Leu Asn Met Phe Pro Val Pro Lys Phe Phe
        115                 120                 125

Pro Leu Asp Gly Gly Arg Tyr Ile Gly Thr Met Val Ser Val Val Leu
    130                 135                 140

Arg Asp Pro Glu Thr Gly Glu Val Asn Leu Gly Thr Tyr Arg Met Gln
145                 150                 155                 160

Met Leu Asp Asp Lys Arg Cys Gly Val Gln Ile Leu Pro Gly Lys Arg
                165                 170                 175

Gly Glu Arg Ile Met Lys Lys Tyr Ala Lys Met Gly Lys Lys Met Pro
            180                 185                 190

Ala Ala Ala Ile Ile Gly Cys Asp Pro Leu Ile Phe Met Ser Gly Thr
        195                 200                 205

Leu Met His Lys Gly Ala Ser Asp Phe Asp Ile Thr Gly Thr Val Arg
    210                 215                 220

Gly Gln Gln Ala Glu Phe Leu Met Ala Pro Leu Thr Gly Leu Pro Val
225                 230                 235                 240
```

```
Pro Ala Gly Ala Glu Ile Val Leu Glu Gly Glu Ile Asp Pro Asn Ala
                245                 250                 255
Phe Leu Pro Glu Gly Pro Phe Ala Glu Tyr Thr Gly Tyr Tyr Thr Asp
                260                 265                 270
Glu Leu His Lys Pro Ile Pro Lys Pro Val Leu Glu Val Gln Gln Ile
                275                 280                 285
Leu His Arg Asn Ser Pro Ile Leu Trp Ala Thr Gly Gln Gly Arg Pro
                290                 295                 300
Val Thr Asp Val His Met Leu Leu Ala Phe Thr Arg Thr Ala Thr Leu
305                 310                 315                 320
Trp Thr Glu Leu Glu Gln Met Arg Ile Pro Gly Ile Gln Ser Val Cys
                325                 330                 335
Val Met Pro Glu Ser Thr Gly Arg Phe Trp Ser Val Val Ser Val Lys
                340                 345                 350
Gln Ala Tyr Pro Gly His Ser Arg Gln Val Ala Asp Ala Val Ile Ala
                355                 360                 365
Ser Asn Thr Gly Ser Tyr Gly Met Lys Gly Val Ile Thr Val Asp Glu
                370                 375                 380
Asp Ile Gln Ala Asp Leu Gln Arg Val Phe Trp Ala Leu Ser Cys
385                 390                 395                 400
Arg Tyr Asp Pro Ala Arg Gly Thr Glu Leu Ile Lys Arg Gly Arg Ser
                405                 410                 415
Thr Pro Leu Asp Pro Ala Leu Asp Pro Asn Gly Asp Lys Leu Thr Thr
                420                 425                 430
Ser Arg Ile Leu Met Asp Ala Cys Ile Pro Tyr Glu Trp Lys Gln Lys
                435                 440                 445
Pro Val Glu Ala Arg Met Asp Glu Met Leu Ala Lys Ile Arg Ala
                450                 455                 460
Arg Trp His Glu Tyr Gly Ile Asp
465                 470

<210> SEQ ID NO 4
<211> LENGTH: 1419
<212> TYPE: DNA
<213> ORGANISM: Thauera aromatica

<400> SEQUENCE: 4
atggacctgc gctacttcat caaccagtgt gccgaagccc acgaactgaa gagaatcacc      60
accgaggtcg attggaatct ggagatttcc catgtttcca agctgaccga agagaaaaaa     120
ggcccggcgc tgctgttcga agcatcaag ggctacgaca cgccggtgtt caccggggcc     180
ttcgcgacca ccaagcgcct cgccgtcatg ctcggcctgc cgcacaacct gtcgctgtgc     240
gaatccgccc agcaatggat gaagaaaacg atcacctccg aagggctgat caaggcgaag     300
gaagtgaagg acgcccggt gctggaaaac gtgctcagcg cgacaaggt cgatctcaac      360 atgttcccgg tgccgaagtt cttccccctc gacggcgggc gctacatcgg cacgatggta     420
tcggtggtgc tgcgtgatcc ggagacgggc gaggtcaacc tcggcaccta ccgcatgcag     480
atgctcgacg acaagcgctg cggggtgcag atcctgcccg ggaagcgcgg cgaacggatc     540
atgaaaaagt acgccaagat gggcaaaaag atgcccgccg cggcgatcat cggctgcgat     600
ccgctgatct tcatgtccgg cacgctgatg cacaagggcg ccagcgactt cgacattacc     660
ggcaccgtgc gcggccagca ggccgagttc ctgatggcgc cgctgaccgg gctgccggtg     720
ccggccgggg ccgagatcgt gctcgaaggc gagatcgatc cgaacgcctt cctgcccgaa     780
```

-continued

```
ggcccgttcg ccgaatacac cggctactac accgacgaac tgcacaagcc gatcccgaaa        840
ccggtgctcg aagtgcagca gatcctgcac cgcaacagcc cgatcctgtg ggccaccggc        900
cagggccgcc cggtgaccga cgtccatatg ctgctcgcct tcacccggac cgcgaccttg        960
tggaccgagc tcgagcagat cgcattccc ggcatccagt cggtgtgcgt gatgccggaa        1020
tcgaccgggc gcttctggtc ggtggtgtcg gtcaagcagg cctacccggg cactcgcgc        1080 caggtggccg acgcggtgat cgccagcaac accggctcgt acggcatgaa gggtgtgatc        1140
acggtcgatg aggacatcca ggccgacgat ctgcagcgcg tgttctgggc gctgtcgtgc        1200
cgctacgacc cggcgcgcgg caccgagctg atcaagcgcg ccgctcgac gccgctcgat        1260 ccggcgctcg acccgaacgg cgacaagctc accacgtcgc ggatcctgat ggacgcctgc        1320
atcccctacg agtggaagca gaagccggtc gaagcgcgca tggacgaaga gatgctggcg        1380
aagatccgcg cccgctggca cgagtacggc atcgactga                              1419
```

<210> SEQ ID NO 5
<211> LENGTH: 612
<212> TYPE: PRT
<213> ORGANISM: Thauera aromatica

<400> SEQUENCE: 5

```
Met Lys Phe Pro Val Pro His Asp Ile Gln Ala Lys Thr Ile Pro Gly
  1               5                  10                  15

Thr Glu Gly Trp Glu Arg Met Tyr Pro Tyr His Tyr Gln Phe Val Thr
                 20                  25                  30

Asp Asp Pro Gln Arg Asn Gln Tyr Glu Lys Glu Thr Phe Trp Phe Tyr
             35                  40                  45

Asp Gly Leu His Tyr Pro Glu Pro Leu Tyr Pro Phe Asp Thr Ile Trp
         50                  55                  60

Asp Glu Ala Trp Tyr Leu Ala Leu Ser Gln Phe Asn Asn Arg Ile Phe
 65                  70                  75                  80

Gln Val Pro Pro Val Arg Gly Val Asp His Arg Ile Ile Asn Gly Tyr
                 85                  90                  95

Val Tyr Ile Ser Pro Val Pro Ile Lys Asp Pro Asp Glu Ile Gly Lys
            100                 105                 110

Arg Val Pro Asn Phe Met Glu Arg Ala Gly Phe Tyr Tyr Lys Asn Trp
        115                 120                 125

Asp Glu Leu Glu Ala Lys Trp Lys Val Lys Met Glu Ala Thr Ile Ala
    130                 135                 140

Glu Leu Glu Ala Leu Glu Val Pro Arg Leu Pro Asp Ala Glu Asp Met
145                 150                 155                 160

Ser Val Val Thr Glu Gly Val Gly Glu Ser Lys Ala Tyr His Leu Leu
                165                 170                 175

Lys Asn Tyr Asp Asp Leu Ile Asn Leu Gly Ile Lys Cys Trp Gln Tyr
            180                 185                 190

His Phe Glu Phe Leu Asn Leu Gly Tyr Ala Ala Tyr Val Phe Phe Met
        195                 200                 205

Asp Phe Ala Gln Lys Leu Phe Pro Ser Ile Pro Leu Gln Arg Val Thr
    210                 215                 220

Gln Met Val Ser Gly Ile Asp Val Ile Met Tyr Arg Pro Asp Asp Glu
225                 230                 235                 240

Leu Lys Glu Leu Ala Lys Lys Ala Val Ser Leu Glu Val Asp Glu Ile
                245                 250                 255

Val Thr Gly His Arg Glu Trp Ser Asp Val Lys Ala Ala Leu Ser Ala
```

-continued

```
                260                 265                 270
His Arg His Gly Ala Glu Trp Leu Glu Ala Phe Glu Lys Ser Arg Tyr
            275                 280                 285
Pro Trp Phe Asn Ile Ser Thr Gly Thr Gly Trp Phe His Thr Asp Arg
        290                 295                 300
Ser Trp Asn Asp Asn Leu Asn Ile Pro Leu Asp Gly Ile Gln Thr Tyr
305                 310                 315                 320
Ile Gly Lys Leu His Ala Gly Val Ala Ile Glu Arg Pro Met Glu Ala
                325                 330                 335
Val Arg Ala Glu Arg Asp Arg Ile Thr Ala Glu Tyr Arg Asp Leu Ile
            340                 345                 350
Asp Ser Asp Glu Asp Arg Lys Gln Phe Asp Glu Leu Leu Gly Cys Ala
        355                 360                 365
Arg Thr Val Phe Pro Tyr Val Glu Asn His Leu Phe Tyr Val Glu His
        370                 375                 380
Trp Phe His Ser Val Phe Trp Asn Lys Met Arg Glu Val Ala Ala Ile
385                 390                 395                 400
Met Lys Glu His Cys Met Ile Asp Asp Ile Glu Asp Ile Trp Tyr Leu
                405                 410                 415
Arg Arg Asp Glu Ile Lys Gln Ala Leu Trp Asp Leu Val Thr Ala Trp
            420                 425                 430
Ala Thr Gly Val Thr Pro Arg Gly Thr Ala Thr Trp Pro Ala Glu Ile
        435                 440                 445
Glu Trp Arg Lys Gly Val Met Gln Lys Phe Arg Glu Trp Ser Pro Pro
        450                 455                 460
Pro Ala Ile Gly Ile Ala Pro Glu Val Ile Gln Glu Pro Phe Thr Ile
465                 470                 475                 480
Val Leu Trp Gly Val Thr Asn Ser Ser Leu Ser Ala Trp Ala Ala Val
                485                 490                 495
Gln Glu Ile Asp Asp Pro Asp Ser Ile Thr Glu Leu Lys Gly Phe Ala
            500                 505                 510
Ala Ser Pro Gly Thr Val Glu Gly Lys Ala Arg Val Cys Arg Ser Ala
        515                 520                 525
Glu Asp Ile Arg Asp Leu Lys Glu Gly Glu Ile Leu Val Ala Pro Thr
        530                 535                 540
Thr Ser Pro Ser Trp Ala Pro Ala Phe Ala Lys Ile Lys Ala Cys Val
545                 550                 555                 560
Thr Asp Val Gly Gly Val Met Ser His Ala Ala Ile Val Cys Arg Glu
                565                 570                 575
Tyr Gly Met Pro Ala Val Val Gly Thr Gly Leu Ser Thr Arg Val Val
            580                 585                 590
Arg Thr Gly Met Thr Leu Arg Val Asp Gly Ser Ser Gly Leu Ile Thr
        595                 600                 605
Ile Ile Thr Asp
610

<210> SEQ ID NO 6
<211> LENGTH: 1839
<212> TYPE: DNA
<213> ORGANISM: Thauera aromatica

<400> SEQUENCE: 6
atgaagtttc ctgttccgca cgacatccag gccaagacga ttccggggac cgaaggctgg      60
gagcggatgt acccgtacca ctaccagttc gtcaccgacg atccgcagcg taaccagtac     120
```

-continued

```
gagaaagaaa ccttctggtt ttacgacgga ttgcattacc cggagccgct ttatccgttc    180
gacacgatct gggacgaggc ctggtatctc gccctgtcgc aattcaacaa tcgaattttc    240
caggtgccgc cggtgcgcgg cgtcgatcac cggatcatca acggttacgt ctatatctcg    300
ccggttccga tcaaggaccc cgatgaaatc ggcaagcgcg tgcccaattt catggagcgc    360
gccggtttct attacaagaa ctgggacgag ctcgaggcga atggaaagt gaagatggag    420 gcgacgatcg ccgagctcga agcgctcgag gttccgcgcc tgcccgacgc cgaagacatg    480
tcggtggtga ccgaaggagt cggtgaatcg aaggcctacc acctgctcaa gaattacgac    540
gacctgatca acctcggcat caagtgctgg caataccact tcgaattcct caatcttggc    600
tatgccgcct acgttttctt catggatttc gcgcagaagc tgtttccgag cattccgctc    660
cagcgcgtca cccagatggt gtcggggatc gacgtcatca tgtaccgccc ggacgacgaa    720
ctgaaggaac tggcaaagaa ggccgtttca ctcgaagtcg atgaaatcgt caccggccat    780
cgggagtgga gcgacgtcaa ggcggcgctt tcggcacacc gccacggtgc cgaatggctc    840
gaagcattcg agaaatcccg ctaccgtgg ttcaacattt cgaccggcac gggatggttc    900
cataccgacc gcagctggaa cgacaacctc aacattccgc tcgacggcat ccagacctat    960
atcggcaagc ttcacgccgg cgtcgccatc gagcggccga tggaagcggt ccgtgccgag   1020
cgcgaccgga tcaccgccga gtaccgcgat ctgatcgaca cgacgaggga ccgcaagcag   1080
ttcgacgaac tgctcggctg cgcccggacg gtgttcccct acgtcgagaa ccatctgttc   1140
tacgtcgagc actggttcca ctcggtgttc tggaacaaga tgcgcgaagt cgctgcgatc   1200
atgaaagaac actgcatgat cgacgacatt gaagacatct ggtatctgcg ccgcgatgaa   1260
atcaagcagg cgctgtggga tctggtcacc gcctgggcaa ccggcgtcac ccctcgcggc   1320
accgccacct ggccggccga aatcgaatgg cgcaaggggg tgatgcagaa gttccgcgaa   1380
tggagcccgc cgccggccat cggcatcgca ccggaagtga tccaggagcc cttcaccatc   1440
gtgctctggg gggtcaccaa cagctcgctc tcggcctggg ccgccgtcca ggaaatcgac   1500
gaccccgaca gcatcaccga gctgaaaggc ttcgccgcca gccgggcac ggtcgaaggc   1560 aaggcgcgcg tgtgccgcag cgccgaagac atccgcgacc tgaaggaggg cgaaattctc   1620
gtcgccccga ccacctcgcc ttcgtgggcg ccggccttcg ccaagatcaa ggcctgcgtc   1680
accgatgtcg gcggcgtcat gagccatgcc gcgatcgtat gccgcgaata cggcatgccg   1740
gcggtggtgg gcaccgggct atcgacccgt gtggtccgca ccggcatgac gctgcgggtc   1800
gatggttcga gcgggctgat cacgatcatc acggattga                         1839
```

<210> SEQ ID NO 7
<211> LENGTH: 169
<212> TYPE: PRT
<213> ORGANISM: Thauera aromatica

<400> SEQUENCE: 7

```
Met Glu Gln Ala Lys Asn Ile Lys Leu Val Ile Leu Asp Val Asp Gly
  1               5                  10                  15

Val Met Thr Asp Gly Arg Ile Val Ile Asn Asp Glu Gly Ile Glu Ser
             20                  25                  30

Arg Asn Phe Asp Ile Lys Asp Gly Met Gly Val Ile Val Leu Gln Leu
         35                  40                  45

Cys Gly Val Glu Val Ala Ile Ile Thr Ser Lys Lys Ser Gly Ala Val
     50                  55                  60
```

-continued

```
Arg His Arg Ala Glu Glu Leu Lys Ile Lys Arg Phe His Glu Gly Ile
 65                  70                  75                  80

Lys Lys Lys Thr Glu Pro Tyr Ala Gln Met Leu Glu Glu Met Asn Ile
                 85                  90                  95

Ser Asp Ala Glu Val Cys Tyr Val Gly Asp Asp Leu Val Asp Leu Ser
                100                 105                 110

Met Met Lys Arg Val Gly Leu Ala Val Ala Val Gly Asp Ala Val Ala
            115                 120                 125

Asp Val Lys Glu Val Ala Ala Tyr Val Thr Thr Ala Arg Gly Gly His
        130                 135                 140

Gly Ala Val Arg Glu Val Ala Glu Leu Ile Leu Lys Ala Gln Gly Lys
145                 150                 155                 160

Trp Asp Ala Met Leu Ser Lys Ile His
                165
```

<210> SEQ ID NO 8
<211> LENGTH: 510
<212> TYPE: DNA
<213> ORGANISM: Thauera aromatica

<400> SEQUENCE: 8

| | |
|---|---|
| atggaacagg cgaagaacat caagctggtg atcctcgacg tcgatggcgt gatgaccgac | 60 |
| gggcgcatcg tgatcaatga cgaaggcatc gagtcgcgca acttcgacat caaggacggc | 120 |
| atgggcgtga tcgtgctgca actgtgcggc gtcgaggtcg cgatcatcac ctcgaagaaa | 180 |
| tccggcgcgg tgcgccatcg cgccgaggag ctgaagatca agcgcttcca cgagggcatc | 240 |
| aagaagaaga ccgagcccta cgcgcagatg ctcgaggaga tgaacatctc cgatgccgaa | 300 |
| gtctgctacg tcggcgacga cctcgtcgat ctgtcgatga tgaagcgcgt cggcctggcc | 360 |
| gtggcggtcg gtgacgccgt ggccgacgtc aaggaagtgg ccgcttatgt gacgactgcg | 420 |
| cgcggcgggc acggcgcggt gcgcgaagtc gcggagctga tcctgaaagc gcagggcaag | 480 |
| tgggacgcga tgctctcgaa gatccattga | 510 |

<210> SEQ ID NO 9
<211> LENGTH: 194
<212> TYPE: PRT
<213> ORGANISM: Thauera aromatica

<400> SEQUENCE: 9

```
Met Arg Ile Val Val Gly Met Ser Gly Ala Ser Gly Ala Ile Tyr Gly
  1               5                  10                  15

Ile Arg Ile Leu Glu Ala Leu Gln Arg Ile Gly Val Glu Thr Asp Leu
                 20                  25                  30

Val Met Ser Asp Ser Ala Lys Arg Thr Ile Ala Tyr Glu Thr Asp Tyr
             35                  40                  45

Ser Ile Ser Asp Leu Lys Gly Leu Ala Thr Cys Val His Asp Ile Asn
         50                  55                  60

Asp Val Gly Ala Ser Ile Ala Ser Gly Ser Phe Arg His Ala Gly Met
 65                  70                  75                  80

Ile Ile Ala Pro Cys Ser Ile Lys Thr Leu Ser Ala Val Ala Asn Ser
                 85                  90                  95

Phe Asn Thr Asn Leu Leu Ile Arg Ala Ala Asp Val Ala Leu Lys Glu
                100                 105                 110

Arg Arg Lys Leu Val Leu Met Leu Arg Glu Thr Pro Leu His Leu Gly
            115                 120                 125
```

```
His Leu Arg Leu Met Thr Gln Ala Thr Glu Asn Gly Ala Val Leu Leu
            130                 135                 140

Pro Pro Leu Pro Ala Phe Tyr His Arg Pro Lys Thr Leu Asp Asp Ile
145                 150                 155                 160

Ile Asn Gln Ser Val Thr Lys Val Leu Asp Gln Phe Asp Leu Asp Val
                165                 170                 175

Asp Leu Phe Gly Arg Trp Thr Gly Asn Glu Glu Arg Glu Leu Ala Lys
            180                 185                 190

Ser Arg

<210> SEQ ID NO 10
<211> LENGTH: 585
<212> TYPE: DNA
<213> ORGANISM: Thauera aromatica

<400> SEQUENCE: 10
atgagaatcg tcgtcggaat gtccggtgcc agcggtgcga tctacggcat ccggatcctc      60
gaggcactac agcgcatcgg tgtcgaaacc gacctggtga tgtcggattc ggccaagcgg     120
accatcgcat acgaaacgga ctattcgatc agcgacttga agggactcgc gacctgcgtc     180
catgacatca atgatgtcgg ggcgtcgatc gccagcggct cgttccgcca tgccggcatg     240
atcatcgcgc cctgttcgat caagaccctg tccgcagtcg ccaactcgtt caacacgaat     300
ctgttgatcc gcgccgccga cgtcgcgttg aaggagcggc gcaagctcgt gctgatgctg     360
cgcgagacgc cgctgcacct gggccacctg cgcctgatga cccaggccac ggagaacggc     420
gcggttctcc tccctcccct gcccgcgttc taccaccgcc ccaagacgct cgacgacatc     480
atcaaccagt cggtgacgaa agtgctcgac cagttcgatc tcgacgtcga tctcttcggg     540
cggtggacgg gcaacgaaga acgcgaactg gcgaaatccc gatag                     585

<210> SEQ ID NO 11
<211> LENGTH: 374
<212> TYPE: PRT
<213> ORGANISM: Thauera aromatica

<400> SEQUENCE: 11

Met Gly Ser Ile Val Ser Thr Val Ala Leu Ser Ala Ala Thr Ala Asp
  1               5                  10                  15

Ser Thr Ser Pro Lys Val Cys Pro Phe Glu Ala Cys Gly Lys Asp Ser
                20                  25                  30

Val Pro Leu Val Gly Gly Lys Cys Ala Ser Leu Gly Glu Leu Ile Asn
            35                  40                  45

Ala Gly Val Arg Val Pro Pro Gly Phe Ala Leu Thr Thr Ser Gly Tyr
     50                  55                  60

Ala Gln Phe Met Arg Glu Ala Gly Ile Gln Ala Asp Ile Gly Ala Leu
 65                  70                  75                  80

Leu Glu Gly Leu Asp His Gln Asp Met Asp Lys Leu Glu Glu Ala Ser
                 85                  90                  95

Arg Ala Ile Arg Glu Met Ile Glu Ser Arg Pro Met Pro Ile Glu Leu
                100                 105                 110

Glu Asp Leu Ile Ala Glu Ala Tyr Arg Lys Leu Ser Val Arg Cys Tyr
            115                 120                 125

Leu Pro Ala Ala Pro Val Ala Val Arg Ser Ser Ala Thr Ala Glu Asp
    130                 135                 140

Leu Pro Gly Ala Ser Phe Ala Gly Gln Gln Asp Thr Tyr Leu Trp Ile
145                 150                 155                 160
```

```
Arg Gly Val Asp Asp Leu Ile His His Val Arg Arg Cys Ile Ser Ser
                165                 170                 175
Leu Tyr Thr Gly Arg Ala Ile Ala Tyr Arg Met Lys Met Gly Phe Pro
            180                 185                 190
His Glu Gln Val Ala Ile Ser Val Gly Val Gln Met Met Ala Asn Ala
        195                 200                 205
Tyr Thr Ala Gly Val Met Phe Thr Ile His Pro Gly Thr Gly Asp Arg
    210                 215                 220
Ser Val Ile Val Ile Asp Ser Asn Phe Gly Phe Gly Glu Ser Val Val
225                 230                 235                 240
Ser Gly Glu Val Thr Pro Asp Asn Phe Val Asn Lys Val Thr Leu
                245                 250                 255
Asp Ile Ile Glu Arg Thr Ile Ser Thr Lys Glu Leu Cys His Thr Val
                260                 265                 270
Asp Leu Lys Thr Gln Lys Ser Val Ala Leu Pro Val Pro Ala Glu Arg
            275                 280                 285
Gln Asn Ile Gln Ser Ile Thr Asp Asp Glu Ile Ser Glu Leu Ala Trp
        290                 295                 300
Ala Ala Lys Lys Ile Glu Lys His Tyr Gly Arg Pro Met Asp Ile Glu
305                 310                 315                 320
Trp Ala Ile Asp Lys Asn Leu Pro Ala Asp Gly Asn Ile Phe Ile Leu
                325                 330                 335
Gln Ala Arg Pro Glu Thr Ile Trp Ser Asn Arg Gln Lys Ala Ser Ala
                340                 345                 350
Thr Thr Gly Ser Thr Ser Ala Met Asp Tyr Ile Val Ser Ser Leu Ile
            355                 360                 365
Thr Gly Lys Arg Leu Gly
    370

<210> SEQ ID NO 12
<211> LENGTH: 1125
<212> TYPE: DNA
<213> ORGANISM: Thauera aromatica

<400> SEQUENCE: 12
atgggaagta tcgtttccac cgtagccctg tccgcggcca ccgccgacag cacttcgccg    60
aaggtctgcc cgttcgaggc ctgcggcaag gactcggtcc cgctggtggg cggcaagtgc   120
gcgtccctgg gcgaactgat caacgccggc gtacgggtgc gccgggcctt tgccctgacc   180
accagcggct atgcccagtt catgcgtgaa gccggcatcc aggcggacat cggcgcgctg   240
ctcgaaggcc tcgaccacca ggacatggac aagctcgagg aagcatcgag ggcgatccgc   300
gaaatgatcg aatcgcgccc gatgccgatc gagctcgaag acctgatcgc gaggcctac    360
cgcaagctgt cggtccgctg ctatctgccc gcggcgccgg tggcggtgcg ttcgagcgcg   420
accgccgagg acctgcccgg tgcgagcttt gccggccagc aggataccta cctgtggatc   480
cgcggcgtcg atgacctcat ccaccacgtc ggcgctgca tctccagcct ctacaccggc    540
cgggcgatcg cctaccggat gaagatgggc ttcccgcacg agcaggtcgc gatcagcgtc   600
ggcgtccaga tgatggcgaa cgcctacacc gcggggggtga tgttcacgat ccatccgggc   660
accggcgacc gctcggtgat cgtcatcgat tcgaatttcg gcttcggtga atccgtggtg   720
tcgggcgaag tcacgccgga caacttcgtc gtcaacaagg tcaccctcga catcatcgag   780
cgcacgattt cgacgaagga gctgtgccac accgtcgatc tgaagaccca gaaatcagtc   840
```

```
gcacttccgg tccctgccga gcgccagaac atccagtcga ttaccgatga cgaaatcagc      900
gaactcgcct gggccgccaa gaagatcgaa aagcattacg gccgcccgat ggacatcgaa      960
tgggcgatcg acaagaacct gcccgcggac ggaaacattt tcatcctcca gcccggcc       1020 gaaacgatct ggagcaaccg ccagaaagcc agcgcgacga ccggcagcac gtcggcgatg     1080
gattacatcg tatcgagcct gatcacgggc aagcggctcg gctag                     1125
```

<210> SEQ ID NO 13
<211> LENGTH: 223
<212> TYPE: PRT
<213> ORGANISM: Thauera aromatica

<400> SEQUENCE: 13

```
Met Ile Val Arg Asn Trp Met Gln Thr Asn Pro Ile Val Leu Thr Gly
  1               5                  10                  15
Asp Thr Leu Leu Ser Glu Ala Lys Arg Ile Phe Ser Glu Ala Asn Ile
             20                  25                  30
His Ala Leu Pro Val Val Asp Asp Gly Arg Leu Arg Gly Leu Ile Thr
         35                  40                  45
Arg Ala Gly Cys Leu Arg Ala Ala His Ala Ala Leu Arg Thr Gln Asp
     50                  55                  60
Thr Asp Glu Leu Asn Tyr Phe Ser Asn Arg Val Lys Val Lys Asp Ile
 65                  70                  75                  80
Met Val Arg Asn Pro Ala Thr Ile Asp Ala Asp Asp Thr Met Glu His
                 85                  90                  95
Cys Leu Gln Val Gly Gln Glu His Gly Val Gly Gln Leu Pro Val Met
            100                 105                 110
Asp Lys Gly Asn Val Val Gly Ile Ile Ser Ala Ile Glu Met Phe Ser
        115                 120                 125
Leu Ala Ala His Phe Leu Gly Ala Trp Glu Lys Arg Ser Gly Val Thr
    130                 135                 140
Leu Ala Pro Ile Asp Leu Lys Gln Gly Thr Met Gly Arg Ile Ile Asp
145                 150                 155                 160
Thr Val Glu Ala Ala Gly Ala Glu Val His Ala Ile Tyr Pro Ile Ser
                165                 170                 175
Ala His Asp Arg Glu Ser Ala Ser Ala Arg Arg Glu Arg Lys Val Ile
            180                 185                 190
Ile Arg Phe His Ala Ala Asn Val Ala Ala Val Ile Glu Ala Leu Ala
        195                 200                 205
His Ala Gly Tyr Glu Val Ile Glu Ala Val Gln Ala Ala His
    210                 215                 220
```

<210> SEQ ID NO 14
<211> LENGTH: 672
<212> TYPE: DNA
<213> ORGANISM: Thauera aromatica

<400> SEQUENCE: 14

```
atgatcgtac gcaactggat gcagaccaat ccgatcgtgc tcaccgggga caccttgctg       60
tccgaagcga agcggatctt ttccgaagcc aatatccacg cattaccggt cgtcgatgac      120
ggccgcctgc gcggactcat caccgcgcc ggctgcctgc gggccgcgca tgccgcgctg       180
cggacccagg acaccgacga gctcaactac ttctcgaacc gggtcaaggt caaggacatc      240
atggtccgca acccggccac catcgatgcc gacgacacga tggaacactg cctgcaggtc      300
ggccaggaac acggcgtcgg ccaattgccg gtgatggaca aaggcaatgt cgtcggaatc      360
```

-continued

```
atttcggcaa tcgaaatgtt ctcgctggcg gcgcatttcc ttggtgcctg ggaaaagcgc    420
agcggcgtca ccctggcccc gatcgatctc aagcagggaa ccatgggccg catcatcgac    480
accgtcgaag ccgccggcgc cgaggtgcac gcgatctacc cgatctcggc ccatgacagg    540
gagtccgcct cggccaggcg ggagcggaaa gtgatcatcc gcttccacgc cgcgaacgtc    600
gcggcagtca tcgaggcgct cgcccacgcc ggctacgaag tcatcgaggc cgttcaagcc    660
gcagcgcatt ga                                                       672
```

<210> SEQ ID NO 15
<211> LENGTH: 357
<212> TYPE: PRT
<213> ORGANISM: Thauera aromatica

<400> SEQUENCE: 15

```
Leu His Arg Ser Arg Arg Gly Thr Arg Pro Arg Ser Lys Glu Val Ile
  1               5                  10                  15

His Arg His Pro Asp Asp Leu Leu Ser Leu Leu Pro Ile Leu Thr His
             20                  25                  30

His Glu Lys Asp Ala Ala Pro Phe Ile Thr Thr Gly Val Val Leu Cys
         35                  40                  45

Thr Asp Pro Glu Thr Gly Arg Arg Gly Met Gly Ile His Arg Met Met
     50                  55                  60

Val Lys Gly Gly Arg Arg Leu Gly Ile Leu Leu Ala Asn Pro Pro Ile
 65                  70                  75                  80

Pro His Phe Leu Ala Lys Ala Glu Ala Ala Gly Lys Pro Leu Asp Val
                 85                  90                  95

Ala Ile Ala Leu Gly Leu Glu Pro Ala Thr Leu Leu Ser Ser Val Val
            100                 105                 110

Lys Val Gly Pro Arg Val Pro Asp Lys Met Ala Ala Gly Ala Leu
        115                 120                 125

Arg Gly Glu Pro Val Glu Leu Val Arg Ala Glu Thr Val Asp Val Asp
    130                 135                 140

Ile Pro Ala Arg Ala Glu Ile Val Ile Glu Gly Arg Ile Leu Pro Gly
145                 150                 155                 160

Val Arg Glu Leu Glu Gly Pro Phe Gly Glu Asn Thr Gly His Tyr Phe
                165                 170                 175

Ser Asn Val Ser Pro Val Ile Glu Ile Ser Ala Val Thr His Arg Asp
            180                 185                 190

Asn Phe Ile Tyr Pro Gly Leu Cys Pro Trp Ser Pro Glu Val Asp Ala
        195                 200                 205

Leu Leu Ser Leu Ala Ala Gly Ala Glu Leu Leu Gly Gln Leu Gln Gly
    210                 215                 220

Leu Ile Asp Gly Val Val Asp Leu Glu Met Ala Gly Gly Thr Ser Gly
225                 230                 235                 240

Phe Ser Val Val Ala Val His Arg Thr Thr Ala Ala Asp Val Arg
                245                 250                 255

Arg Leu Val Met Leu Ala Leu Asn Leu Asp Arg Arg Leu Lys Thr Ile
            260                 265                 270

Thr Val Val Asp Asp Val Asp Ile Arg Asp Pro Arg Glu Val Ala
        275                 280                 285

Trp Ala Met Ala Thr Arg Tyr Gln Pro Ala Arg Asp Thr Val Val Ile
    290                 295                 300

His Gly Cys Glu Ala Tyr Val Ile Asp Pro Ser Ala Thr Gly Asp Gly
```

```
                305                 310                 315                 320
Thr Ser Lys Val Gly Phe Ile Ala Thr Arg Ala Ser Gly Ala Asp Ser
            325                 330                 335

Asp Arg Ile Thr Leu Pro Pro Ala Ala Leu Ala Lys Ala Arg Ala Ile
        340                 345                 350

Ile Ala Arg Leu His
        355
```

<210> SEQ ID NO 16
<211> LENGTH: 1074
<212> TYPE: DNA
<213> ORGANISM: Thauera aromatica

<400> SEQUENCE: 16

```
ttgcaccgat ccaggcgcgg gacgcggccc cggtcaaagg aagtgatcca ccgccatccg      60
gacgatctgc tgtcgctgct gccgatcctg acccaccacg aaaaggatgc ggccccttc     120
atcaccaccg gcgtggtgtt gtgcaccgac cccgagaccg gccggcgcgg catgggcatc    180
caccgcatga tggtcaaggg cgggcgccgg ctcggcatcc tgctcgccaa tccgccgatt    240
ccgcatttcc tcgccaaggc cgaagcggcc ggcaagccgc tcgatgtcgc catcgcgctc    300
ggtctcgaac ccgccaccct gctgtcgtcg gtggtcaagg tcggcccgcg ggtgcccgac    360
aagatggccg ctgccggcgc cctgcgtggc gaaccggtcg agctggtgcg cgccgaaacg    420
gtggatgtgg acatcccggc gcgcgccgaa atcgtcatcg aaggccggat tctgccgggc    480
gtgcgcgaac tcgagggccc gttcggggag aacaccgggc actattttc caacgtcagc    540
ccggtcatcg agatcagcgc cgtcacccat cgcgacaact tcatctaccc gggcctgtgc    600
ccatggtcgc ccgaggtcga tgcgctgctg tcgctggcgg ccggtgccga attgctcggc    660
cagttgcagg ggctgatcga cggcgtcgtc gatctggaga tggccggcgg caccagcggc    720
ttttccgtgg ttgtcgcagt ccatcggacc actgcggccg acgtcagacg gctggtcatg    780
ctcgcgctca atctcgaccg ccgcctgaag acgatcaccg tcgtcgacga cgacgtcgac    840
atccgcgacc cgcgcgaagt cgcctgggcc atggctaccc gctaccagcc cgcccgggac    900
acggtcgtga tccacggctg cgaagcctat gtcatcgatc cttcggcgac cggggacggc    960
acatcgaaag tcgggttcat cgccacccgt gccagcggcc cggactcgga ccgcatcacc   1020
ctgccgccgg cagcgctcgc gaaggcgcgc gccatcatcg ccagactgca ttga          1074
```

<210> SEQ ID NO 17
<211> LENGTH: 143
<212> TYPE: PRT
<213> ORGANISM: Thauera aromatica

<400> SEQUENCE: 17

```
Met Pro Pro Ile Ala Leu Pro Leu Ser Leu Glu Gly Val Val Cys Thr
  1               5                  10                  15

Gly Leu Gly Ala Gly Ala Gln Phe Thr Thr Leu Asp Trp Val Asp
             20                  25                  30

Glu Cys Arg Glu Lys Leu Gly Phe Ile Pro Trp Pro Gly Thr Phe Asn
         35                  40                  45

Val Arg Thr Gln Gly Ala Leu Ala Gly Val Asp Arg Thr Arg Leu Leu
     50                  55                  60

Arg Ser Gly Tyr Ser Ile Arg Ile Arg Pro Ala Pro Gly Tyr Cys Ala
 65                  70                  75                  80

Ala Glu Cys Leu Val Val Asn Ile Ala Gly Arg Ile Ser Gly Ala Val
```

-continued

```
                        85                  90                  95
Leu Phe Pro Glu Val Pro Gly Tyr Pro Asp Gly Gln Leu Glu Ile Ile
                100                 105                 110

Ala Pro Val Pro Val Arg Arg Thr Leu Gly Leu Asn Asp Gly Asp Arg
        115                 120                 125

Val Asn Leu Ser Ile Gly Ile Ser Thr Ser Leu Phe Cys Arg Ala
130                 135                 140

<210> SEQ ID NO 18
<211> LENGTH: 432
<212> TYPE: DNA
<213> ORGANISM: Thauera aromatica

<400> SEQUENCE: 18
atgccaccga tcgcccttcc cctgtcactc gaaggcgtcg tctgcacggg actcggtgca      60
ggcgcgcagt tcaccaccct cgactgggtc gtcgatgaat gccgggaaaa gctcggcttc     120 atccctggc ccggcacctt caacgtgagg acgcagggcg cgcttgcggg cgtggaccgc      180
acccgcctcc tgcgctcggg atacagcatc cgcatccggc cggcgcccgg ctactgtgcc     240
gcggaatgcc tcgtggtcaa catcgcgggg cggatctccg gcgcggtgct attcccagag     300
gtgcccggct acccggacgg ccagctcgaa atcatcgctc cggtgccggt acgaagaacc     360
ctcggcctca atgacggcga ccgggtcaac ctctccatcg gcatcagcac ctccctttc     420 tgccgggcct ga                                                         432

<210> SEQ ID NO 19
<211> LENGTH: 182
<212> TYPE: PRT
<213> ORGANISM: Thauera aromatica

<400> SEQUENCE: 19

Met Ala Pro Lys Phe Cys Pro Gln Cys Gly Thr Ala Leu Val Leu Ala
1               5                   10                  15

Thr Ile His Gly Arg Glu Arg Glu Thr Cys Pro Ala Cys Gly Glu Thr
            20                  25                  30

Phe Phe His Lys Pro Ala Pro Val Val Leu Ala Val Ile Glu His Ala
        35                  40                  45

Gly Gln Leu Val Leu Ile Arg Arg Lys Leu Asp Pro Leu Ala Gly Tyr
    50                  55                  60

Trp Ala Pro Pro Gly Gly Tyr Val Glu Arg Gly Glu Ser Leu Glu Glu
65                  70                  75                  80

Ala Val Val Arg Glu Ala Arg Glu Glu Ser Gly Leu Glu Val Ala Val
                85                  90                  95

Asp Glu Leu Ile Gly Val Tyr Ser Gln Ala Asp Val Arg Ala Val Ile
                100                 105                 110

Leu Ala Tyr Arg Ala His Ser Ile Gly Gly Glu Pro Val Ala Gly Asp
        115                 120                 125

Asp Ala Gly Glu Ile Cys Leu Val Ala Pro Gly Gln Leu Pro Val Gln
    130                 135                 140

Arg Pro Pro Gln Ser Gly Ile Pro Ile Glu His Trp Phe Phe Ser Val
145                 150                 155                 160

Val Glu Glu Val Thr Asp Pro Trp Lys Trp Gly Arg Arg Asn Ser Ala
                165                 170                 175

Lys Lys Met Met Arg Arg
            180
```

-continued

<210> SEQ ID NO 20
<211> LENGTH: 549
<212> TYPE: DNA
<213> ORGANISM: Thauera aromatica

<400> SEQUENCE: 20

| | | |
|---|---|---|
| atggcaccga agttctgccc gcaatgcggc accgccctgg tcctggcgac gatccatggg | 60 |
| cgcgaacgtg aaacctgtcc ggcctgtggc gaaacctttt tccacaagcc cgcgcccgtc | 120 |
| gtgctggcgg tgatcgagca cgccgggcaa ctcgtgctga tccgccgcaa gctcgatccg | 180 |
| ctcgccggct actgggcacc gccgggcggc tacgtcgaac gcggcgaatc gctcgaggag | 240 |
| gcggtcgtac gcgaggcgcg cgaggaaagc ggactcgagg tcgccgtcga tgaactgatc | 300 |
| ggcgtgtatt cgcaggccga cgtgcgcgcg gtgatcctcg cctaccgcgc gcactcgatc | 360 |
| ggcggcgaac cggtcgccgg cgacgacgcc ggcgagatct gcctcgtcgc ccgggccag | 420 |
| ctgccggtgc agcgcccgcc gcagagcggc ataccgatcg aacactggtt tttcagcgta | 480 |
| gtggaggaag tcaccgatcc atggaagtgg gggcgccgca acagcgccaa gaaaatgatg | 540 |
| aggagatag | 549 |

<210> SEQ ID NO 21
<211> LENGTH: 582
<212> TYPE: PRT
<213> ORGANISM: Thauera aromatica

<400> SEQUENCE: 21

Met Ala Lys Leu His Asp Met Ser Cys Ile Asp Gly Gly Asp Leu Arg
1               5                   10                  15

Ser Arg Ile His Phe Cys Ala Asp Thr Gly Gln Ile Trp Leu His Glu
            20                  25                  30

His Arg Met Leu Leu Val His Ala Glu Ala Gln Ala Ala Leu Arg Lys
        35                  40                  45

Glu Leu Ile Asp Thr Leu Gly Met Ala Arg Ala Arg Gly Leu Leu Leu
    50                  55                  60

Arg Met Gly Phe Ala Ser Gly Ala Arg Asp Ala Glu Leu Ala Gln Thr
65                  70                  75                  80

Arg Ile Arg Thr Gly Asp Asp Leu Ala Ala Phe Met Thr Gly Pro Gln
                85                  90                  95

Leu His Ala Leu Glu Gly Ile Val Gly Val Ile Pro Leu Gln Leu Glu
            100                 105                 110

Phe Asp Arg Ala Ala Gly Thr Phe Asn Ala Glu Phe Arg Trp Ile Asn
        115                 120                 125

Ser Trp Glu Gly Gln Ser His Lys Arg His Phe Gly Thr Cys Ser Glu
    130                 135                 140

Pro Val Cys Trp Thr Gln Ile Gly Tyr Ala Cys Gly Tyr Ser Thr Ala
145                 150                 155                 160

Phe Met Gly Arg Pro Ile Leu Tyr Lys Glu Ala Glu Cys Ala Gly Met
                165                 170                 175

Gly Ala Glu His Cys His Ile Val Gly Lys Pro Ala Glu Glu Trp Pro
            180                 185                 190

Asp Ala Glu Tyr Arg Arg Leu Phe Ala Pro Glu Ser Ile Ala Glu
        195                 200                 205

Gln Leu Ile Asp Leu Gln Ala Gln Val Glu Gln Leu Arg Ser Thr Ile
    210                 215                 220

Asp Glu Arg Ala Arg Leu Pro Gly Asp Met Ile Gly Asp Ser Pro Gly

```
                     225                 230                 235                 240
      Phe Arg Phe Ala Leu Ser Leu Leu Gln Gln Ala Ala Gly Ser Ser Ile
                          245                 250                 255
      Ala Ile Leu Leu Leu Gly Glu Thr Gly Val Gly Lys Glu Leu Phe Thr
                  260                 265                 270
      Arg Ala Leu His Glu Met Ser Ala Arg Arg Asp Arg Pro Leu Val Ala
                  275                 280                 285
      Ile Asn Cys Ala Ala Ile Pro His Asp Leu Val Glu Ala Glu Leu Phe
                  290                 295                 300
      Gly Val Glu Lys Gly Ala Tyr Thr Gly Ala Leu Ala Ala Arg Pro Gly
      305                 310                 315                 320
      Arg Phe Glu Arg Ala Asn Gly Gly Thr Leu Phe Leu Asp Glu Ile Gly
                          325                 330                 335
      Asp Leu Pro Leu Thr Ala Gln Ser Lys Leu Leu Arg Val Leu Gln Glu
                  340                 345                 350
      Gly Glu Val Glu Arg Leu Gly Asp Asp Lys Thr Arg Arg Ile Asp Val
                  355                 360                 365
      Arg Leu Val Ala Ala Thr Asn Ala Ser Leu Ala Gln Leu Val Lys Glu
          370                 375                 380
      Gly Arg Phe Arg Ala Asp Leu Tyr Tyr Arg Leu Asn Ala Phe Gln Ile
      385                 390                 395                 400
      Asp Ile Pro Pro Leu Arg Gln Arg Arg Glu Asp Ile Ser Pro Leu Ala
                          405                 410                 415
      Lys His Phe Leu Arg Lys Tyr Ala Ala Ile Asn Gly Lys Lys Leu Leu
                  420                 425                 430
      Gly Phe Ser Asp Lys Ala Lys Lys Ala Leu Val Gly His Ala Trp Pro
                  435                 440                 445
      Gly Asn Ile Arg Glu Leu Gln Asn Thr Val Glu Arg Gly Val Ile Leu
                  450                 455                 460
      Ala Pro Asn Gly Gly Arg Val Glu Val Asp His Leu Phe Leu Ser Gly
      465                 470                 475                 480
      Ala His Ile Glu Asp Glu Asp Gly Phe Gly Leu Gly Pro Asn Gly Lys
                          485                 490                 495
      Ile Asp Thr Glu Gln Asp Ser Leu Ala Arg Ser Leu Cys Ser Ala Val
                  500                 505                 510
      Cys Asp Gly Ala Leu Thr Leu Glu Gln Ile Glu Thr Thr Leu Leu Glu
                  515                 520                 525
      Thr Ala Leu Asp Lys Ala Arg Gly Asn Leu Ser Ser Ala Ala Arg Met
          530                 535                 540
      Leu Gly Leu Thr Arg Pro Gln Phe Ala Tyr Arg Leu Lys Arg Leu Arg
      545                 550                 555                 560
      Gly Glu Glu Ser Gly Ala Gly Pro Gly Ala Asp Val Thr Asp Thr Leu
                          565                 570                 575
      Ser Gly Arg Ala His Ala
                  580

<210> SEQ ID NO 22
<211> LENGTH: 1749
<212> TYPE: DNA
<213> ORGANISM: Thauera aromatica

<400> SEQUENCE: 22
tcatgcgtgc gccctcccgg acagggtgtc ggtcacgtca gctccgggac cggcaccact    60
ttcttcaccg cgcagacgct tgaggcggta ggcgaattgc ggccgggtca ggccgagcat   120
```

```
gcgcgccgcc gaagacaggt tgccgcgcgc cttgtcgagc gcggtttcga gcagggtggt    180
ctcgatctgc tcgagggtca gggcaccatc gcacaccgcg ctgcacaggc tgcgcgccag    240
gctgtcctgt tcggtgtcga tctttccgtt cggcccgagg ccgaacccgt cttcatcctc    300
gatgtgcgca ccggacagga aaaggtggtc cacttcgacc cggccgccgt tcggcgcaag    360
gatcaccccg cgttccaccg tgttctgcag ttcgcggatg ttgcccggcc aggcatggcc    420
gaccagcgcc ttcttcgcct tgtcggaaaa tccgagcagc ttcttgccgt tgatcgccgc    480
atatttcctg aggaaatgct tggccagagg ggagatgtcc tccctgcgct ggcgcagcgg    540
cggaatgtcg atctggaaag cattgagacg gtagtacagg tcggccctga aacgcccttc    600
cttcaccaac tgggcgaggc tggcattggt cgcggcgacg aggcggacgt cgatacggcg    660
ggtcttgtca tcgcccaaac gctcgacctc gccttcctgg agcaccgca gcagcttgct    720
ctgcgccgtc agcggcagat cgccgatttc gtccaggaac agggtgccgc cgttggcgcg    780
ctcgaacctg cccgggcggg ctgccagcgc gccggtgtat gccccttttt ccacgccgaa    840
aagctcggcc tccacgaggt cgtgcggaat cgcggcgcag ttgatcgcaa ccagcgggcg    900
atcgcggcgg gcgctcattt cgtgcagcgc gcgcgtgaac agttccttgc cgaccccgt     960
ttcgccgagc agcaaaatgg cgatgctgct gcccgcggcc tgctgcagca agctgagcgc   1020
gaaccggaac ccgggcgagt cgccgatcat gtcgccaggc agcctggcgc gttcatcgat   1080
cgtggagcgc agctgttcca cctgggcctg caggtcgatc agttgctcgg cgatcgattc   1140
gggggcgaac aggcgtctgt attcctcggc atccggccat tcctcggccg gcttgccgac   1200
gatgtggcaa tgctcggcac ccatgcccgc gcactcggct tccttgtaca ggatcggtcg   1260
ccccatgaag gccgtggagt agccgcaggc atagccgatc tgggtccagc acaccggttc   1320
cgagcaggtt ccgaagtggc gcttgtgcga ctgcccctcc cacgaattga tccagcggaa   1380
ctcggcattg aaggtgccgg cggcgcggtc gaattccagc tggagcggga tgacgccgac   1440
aatgccctcg agcgcgtgca gctgcggccc ggtcatgaat gccgcaaggt cgtcgccggt   1500
cctgatccgt gtctgcgcga gctccgcatc acgggcaccg gatgcgaacc ccatgcgcag   1560
cagcaacccg cgcgcgcgcg ccatgccgag cgtatcgatc agctccttgc gcaaggccgc   1620
ctgcgcctcg gcgtgcacga gcagcatccg atgctcatga gccagatct gcccggtatc   1680
ggcgcagaaa tggatgcgcg accggagatc accgccgtct atgcagctca tatcgtgaag   1740
cttggccat                                                          1749

<210> SEQ ID NO 23
<211> LENGTH: 14272
<212> TYPE: DNA
<213> ORGANISM: Thauera aromatica
<400> SEQUENCE: 23
cggtcgcggt gatgaagcgg accttgttcc tgggcgtgta cgcggcaggc ctgcttgtgg     60
cgctcggatc ggtcatcggg gtgcctccgg gcagaaagcc gtgcctcccc gtaatcctag    120
agattccgcc ccgccttcgc caccgctgtc gcggcggacg cgcacggcgc gcggaatgcg    180
gcgcgccggc atccggggc ggcgcccggc cggcgcgga tcatggcctg ccgtcgcggc    240
agtcgatctc gtcccggtgg ccgaagccgc gcgagttgtc gatgaaatac agccgttcgg    300
gcacgaaacg gtaccagtgc accttcgcca gggcctgcag gatcgcggcc ggcgcacccc    360
ccagcgtgcc gacgacgggg tatttcgccc cgtagagcgc gcgcgcctgc cctgcggcat    420
```

-continued

| | | |
|---|---|---|
| cgccggacag ttccacgaca tggccttcgg cctggatgcc cttgacctca cgccagtcgg | 480 |
| agcagtcctc ctggatggtc accgcggcac gcccatcgcg cgcgatgttg ctgctgtggc | 540 |
| gggcgcctgg cttggacagg aagtacaggt cgaaaccgtc gctggcgtaa acaccgccg | 600 |
| ccgcccacac cccctgctcg ccctgcgtcg ccagcgtcat cgtgtggtgc gcgcgcagcc | 660 |
| agtcgaggac atgggcctgg tgcccgttca tgcgtgcgcc ctcccggaca gggtgtcggt | 720 |
| cacgtcagct ccgggaccgg caccactttc ttcaccgcgc agacgcttga ggcggtaggc | 780 |
| gaattgcggc cgggtcaggc cgagcatgcg cgccgccgaa gacaggttgc cgcgcgcctt | 840 |
| gtcgagcgcg gtttcgagca gggtggtctc gatctgctcg agggtcaggg caccatcgca | 900 |
| caccgcgctg cacaggctgc gcgccaggct gtcctgttcg gtgtcgatct ttccgttcgg | 960 |
| cccgaggccg aaccgtctt catcctcgat gtgcgcaccg gacaggaaaa ggtggtccac | 1020 |
| ttcgaccccgg ccgccgttcg gcgcaaggat caccccgcgt tccaccgtgt tctgcagttc | 1080 |
| gcggatgttg cccggccagg catggccgac cagcgccttc ttcgccttgt cggaaaatcc | 1140 |
| gagcagcttc ttgccgttga tcgccgcata tttcctgagg aaatgcttgg ccagaggga | 1200 |
| gatgtcctcc ctgcgctggc gcagcggcgg aatgtcgatc tggaaagcat tgagacggta | 1260 |
| gtacaggtcg gccctgaaac gcccttcctt caccaactgg gcgaggctgg cattggtcgc | 1320 |
| ggcgacgagg cggacgtcga tacggcgggt cttgtcatcg cccaaacgct cgacctcgcc | 1380 |
| ttcctggagc acccgcagca gcttgctctg cgccgtcagc ggcagatcgc cgatttcgtc | 1440 |
| caggaacagg gtgccgccgt tggcgcgctc gaacctgccc gggcgggctg ccagcgcgcc | 1500 |
| ggtgtatgcc ccttttccca cgccgaaaag ctcggcctcc acgaggtcgt gcggaatcgc | 1560 |
| ggcgcagttg atcgcaacca gcgggcgatc gcggcgggcc ctcatttcgt gcagcgcgcg | 1620 |
| cgtgaacagt tccttgccga ccccgtttc gccgagcagc aaaatggcga tgctgctgcc | 1680 |
| cgcggcctgc tgcagcaagc tgagcgcgaa ccggaacccg ggcgagtcgc cgatcatgtc | 1740 |
| gccaggcagc ctggcgcgtt catcgatcgt ggagcgcagc tgttccacct gggcctgcag | 1800 |
| gtcgatcagt tgctcggcga tcgattcggg ggcgaacagg cgtctgtatt cctcggcatc | 1860 |
| cggccattcc tcggccggct tgccgacgat gtggcaatgc tcggcaccca tgcccgcgca | 1920 |
| ctcggcttcc ttgtacagga tcggtcgccc catgaaggcc gtggagtagc cgcaggcata | 1980 |
| gccgatctgg gtccagcaca ccggttccga gcaggttccg aagtggcgct tgtgcgactg | 2040 |
| cccctcccac gaattgatcc agcggaactc ggcattgaag gtgccggcgg cgcggtcgaa | 2100 |
| ttccagctgg agcgggatga cgccgacaat gccctcgagc gcgtgcagct gcggcccggt | 2160 |
| catgaatgcc gcaaggtcgt cgccggtcct gatccgtgtc tgcgcgagct ccgcatcacg | 2220 |
| ggcaccggat gcgaacccca tgcgcagcag caacccgcgc gcgcgcgcca tgccgagcgt | 2280 |
| atcgatcagc tccttgcgca aggccgcctg cgcctcggcg tgcacgagca gcatccgatg | 2340 |
| ctcatgaagc cagatctgcc cggtatcggc gcagaaatgg atgcgcgacc ggagatcacc | 2400 |
| gccgtctatg cagctcatat cgtgaagctt ggccatcacc cttcctcctg aactggtcct | 2460 |
| tttacgcgca gccaccacgg gtcgtattga cgtgcgtcaa acgcccggc gcgcgactgc | 2520 |
| gcagcgccga aaacgaagag aagccccctgc gttcatctaa tggtcaatcc tgcagccggc | 2580 |
| cggaaggaga actgatcatt tgatgaatcg catccaatgg ccgcttttc caattacccg | 2640 |
| gcacaaacgc cccgccagaa atttattttt tgcaactgca tgaaatgctc gaaaggcctg | 2700 |
| cacaacgggc aaacagcgct cccggcgtat gcgcccgaag gctgaattgc tgctctgccg | 2760 |
| caattaatcg tggcacaccc tttgcattgg atgcctggca ggcgtcgtcc aacaaatccg | 2820 |

```
gtcgcaacga tcgacaacgg aaatagcaaa ggaggggcat cagatgaagt tcctgttcc    2880 gcacgacatc caggccaaga cgattccggg gaccgaaggc tgggagcgga tgtacccgta    2940
ccactaccag ttcgtcaccg acgatccgca gcgtaaccag tacgagaaag aaaccttctg    3000
gttttacgac ggattgcatt acccggagcc gctttatccg ttcgacacga tctgggacga    3060
ggcctggtat ctcgccctgt cgcaattcaa caatcgaatt ttccaggtgc cgccggtgcg    3120
cggcgtcgat caccggatca tcaacggtta cgtctatatc tcgccggttc cgatcaagga    3180
ccccgatgaa atcggcaagc gcgtgcccaa tttcatggag cgcgccggtt tctattacaa    3240
gaactgggac gagctcgagg cgaaatggaa agtgaagatg gaggcgacga tcgccgagct    3300
cgaagcgctc gaggttccgc gcctgcccga cgccgaagca atgtcggtgg tgaccgaagg    3360
agtcggtgaa tcgaaggcct accacctgct caagaattac gacgacctga tcaacctcgg    3420
catcaagtgc tggcaatacc acttcgaatt cctcaatctt ggctatgccg cctacgtttt    3480
cttcatggat ttcgcgcaga agctgtttcc gagcattccg ctccagcgcg tcacccagat    3540
ggtgtcgggg atcgacgtca tcatgtaccg cccggacgac gaactgaagg aactggcaaa    3600
gaaggccgtt tcactcgaag tcgatgaaat cgtcaccggc catcgggagt ggagcgacgt    3660
caaggcggcg ctttcggcac accgccacgt gccgaatgg ctcgaagcat tcgagaaatc    3720
ccgctacccg tggttcaaca tttcgaccgg cacgggatgg ttccataccg accgcagctg    3780
gaacgacaac ctcaacattc cgctcgacgg catccagacc tatatcggca agcttcacgc    3840
cggcgtcgcc atcgagcggc cgatggaagc ggtccgtgcc gagcgcgacc ggatcaccgc    3900
cgagtaccgc gatctgatcg acagcgacga ggaccgcaag cagttcgacg aactgctcgg    3960
ctgcgcccgg acggtgttcc cctacgtcga gaaccatctg ttctacgtcg agcactggtt    4020
ccactcggtg ttctggaaca agatgcgcga agtcgctgcg atcatgaaag aacactgcat    4080
gatcgacgac attgaagaca tctggtatct gcgccgcgat gaaatcaagc aggcgctgtg    4140
ggatctggtc accgcctggg caaccggcgt caccccctcgc ggcaccgcca cctggccggc    4200
cgaaatcgaa tggcgcaagg gggtgatgca gaagttccgc gaatggagcc cgccgccggc    4260
catcggcatc gcaccggaag tgatccagga gccccttcacc atcgtgctct gggggtcac    4320 caacagctcg ctctcggcct gggccgccgt ccaggaaatc gacgaccccg acagcatcac    4380
cgagctgaaa ggcttcgccg ccagcccggg cacggtcgaa ggcaaggcgc gcgtgtgccg    4440
cagcgccgaa gacatccgcg acctgaagga gggcgaaatt ctcgtcgccc cgaccacctc    4500
gccttcgtgg gcgccggcct tcgccaagat caaggcctgc gtcaccgatg tcggcggcgt    4560
catgagccat gccgcgatcg tatgccgcga atacggcatg ccggcggtgg tgggcaccgg    4620
gctatcgacc cgtgtggtcc gcaccggcat gacgctgcgg gtcgatggtt cgagcgggct    4680
gatcacgatc atcacggatt gagggagtga ctgacatggg aagtatcgtt tccaccgtag    4740
ccctgtccgc ggccaccgcc gacagcactt cgccgaaggt ctgcccgttc gaggcctgcg    4800
gcaaggactc ggtcccgctg gtgggcggca agtcgcgtc cctgggcgaa ctgatcaacg    4860
ccggcgtacg ggtgccgccg ggctttgccc tgaccaccag cggctatgcc cagttcatgc    4920
gtgaagccgg catccaggcg gacatcgcg cgctgctcga aggcctcgac caccaggaca    4980
tggacaagct cgaggaagca tcgagggcga tccgcgaaat gatcgaatcg cgcccgatgc    5040
cgatcgagct cgaagacctg atcgccgagg cctaccgcaa gctgtcggtc cgctgctatc    5100
tgcccgcggc gccggtggcg gtgcgttcga gcgcgaccgc cgaggacctg cccggtgcga    5160
```

```
gctttgccgg ccagcaggat acctacctgt ggatccgcgg cgtcgatgac ctcatccacc    5220
acgtccggcg ctgcatctcc agcctctaca ccggccgggc gatcgcctac cggatgaaga    5280
tgggcttccc gcacgagcag gtcgcgatca cgtcggcgt ccagatgatg gcgaacgcct    5340
acaccgcggg ggtgatgttc acgatccatc cgggcaccgg cgaccgctcg gtgatcgtca    5400
tcgattcgaa tttcggcttc ggtgaatccg tggtgtcggg cgaagtcacg ccggacaact    5460
tcgtcgtcaa caaggtcacc ctcgacatca tcgagcgcac gatttcgacg aaggagctgt    5520
gccacaccgt cgatctgaag acccagaaat cagtcgcact tccggtccct gccgagcgcc    5580
agaacatcca gtcgattacc gatgacgaaa tcagcgaact cgcctgggcc gccaagaaga    5640
tcgaaaagca ttacgccgc ccgatggaca tcgaatgggc gatcgacaag aacctgcccg    5700
cggacggaaa cattttcatc ctccaggccc ggcccgaaac gatctggagc aaccgccaga    5760
aagccagcgc gacgaccggc agcacgtcgg cgatggatta tcgtatcg agcctgatca    5820 cgggcaagcg gctcggctag gaggacgaaa aaatgatcgt acgcaactgg atgcagacca    5880
atccgatcgt gctcaccggg gacaccttgc tgtccgaagc gaagcggatc ttttccgaag    5940
ccaatatcca cgcattaccg gtcgtcgatg acggccgcct gcgcggactc atcacccgcg    6000
ccggctgcct gcgggccgcg catgccgcgc tgcggaccca ggacaccgac gagctcaact    6060
acttctcgaa ccgggtcaag gtcaaggaca tcatggtccg caacccggcc accatcgatg    6120
ccgacgacac gatggaacac tgcctgcagg tcggccagga acacgcgtc ggccaattgc    6180 cggtgatgga caaaggcaat gtcgtcggaa tcatttcggc aatcgaaatg ttctcgctgg    6240
cggcgcattt ccttggtgcc tgggaaaagc gcagcggcgt caccctggcc ccgatcgatc    6300
tcaagcaggg aaccatgggc cgcatcatcg acaccgtcga agccgccggc gccgaggtgc    6360
acgcgatcta cccgatctcg gcccatgaca gggagtccgc ctcggccagg cgggagcgga    6420
aagtgatcat ccgcttccac gccgcgaacg tgcggcagt catcgaggcg ctcgcccacg    6480
ccggctacga agtcatcgag gccgttcaag ccgcagcgca ttgagcccag ccccacccat    6540
cctgcctcac cccggtttca cccatttctg ccaaggagcg acaccatgg acctgcgcta    6600 cttcatcaac cagtgtgccg aagcccacga actgaagaga atcaccaccg aggtcgattg    6660
gaatctggag atttccccatg tttccaagct gaccgaagag aaaaaaggcc cggcgctgct    6720
gttcgaaagc atcaagggct acgacacgcc ggtgttcacc ggggccttcg cgaccaccaa    6780
gcgcctcgcc gtcatgctcg gcctgccgca caacctgtcg ctgtgcgaat ccgcccagca    6840
atggatgaag aaaacgatca cctccgaagg gctgatcaag gcgaaggaag tgaaggacgg    6900
cccggtgctg gaaaacgtgc tcagcggcga caaggtcgat ctcaacatgt tcccggtgcc    6960
gaagttcttc ccctcgacg gcgggcgcta catcggcacg atggtatcgg tggtgctgcg    7020
tgatccggag acgggcgagg tcaacctcgg cacctaccgc atgcagatgc tcgacgacaa    7080
gcgctgcggg gtgcagatcc tgcccgggaa gcgcggcgaa cggatcatga aaagtacgc    7140 caagatgggc aaaaagatgc cgccgcggc gatcatcggc tgcgatccgc tgatcttcat    7200
gtccggcacg ctgatgcaca agggcgccag cgacttcgac attaccggca ccgtgcgcgg    7260
ccagcaggcc gagttcctga tgcgccgct gaccgggctg ccggtgccgg ccggggccga    7320
gatcgtgctc gaaggcgaga tcgatccgaa cgccttcctg cccgaaggcc gttcgccga    7380 atacaccggc tactacaccg acgaactgca caagccgatc ccgaaaccgg tgctcgaagt    7440
gcagcagatc ctgcaccgca acagcccgat cctgtgggcc accggccagg gccgcccggt    7500
gaccgacgtc catatgctgc tcgccttcac ccggaccgcg accttgtgga ccgagctcga    7560
```

-continued

```
gcagatgcgc attcccggca tccagtcggt gtgcgtgatg ccggaatcga ccggcgctt      7620 ctggtcggtg gtgtcggtca agcaggccta cccggggcac tcgcgccagg tggccgacgc     7680
ggtgatcgcc agcaacaccg gctcgtacgg catgaagggt gtgatcacgg tcgatgagga     7740
catccaggcc gacgatctgc agcgcgtgtt ctgggcgctg tcgtgccgct acgacccggc     7800
gcgcggcacc gagctgatca agcgcggccg ctcgacgccg ctcgatccgg cgctcgaccc     7860
gaacggcgac aagctcacca cgtcgcggat cctgatggac gcctgcatcc cctacgagtg     7920
gaagcagaag ccggtcgaag cgcgcatgga cgaagagatg ctggcgaaga tccgcgcccg     7980
ctggcacgag tacggcatcg actgagccct tagccgcatg acaaaccacg gccgccgatg     8040
gggcggccgt cactggagga catggagaca tggaacaggc gaagaacatc aagctggtga     8100
tcctcgacgt cgatggcgtg atgaccgacg gcgcatcgt gatcaatgac gaaggcatcg      8160
agtcgcgcaa cttcgacatc aaggacggca tgggcgtgat cgtgctgcaa ctgtgcggcg     8220
tcgaggtcgc gatcatcacc tcgaagaaat ccggcgcggt gcgccatcgc gccgaggagc     8280
tgaagatcaa gcgcttccac gagggcatca agaagaagac cgagccctac gcgcagatgc     8340
tcgaggagat gaacatctcc gatgccgaag tctgctacgt cggcgacgac ctcgtcgatc     8400
tgtcgatgat gaagcgcgtc ggcctggccg tggcggtcgg tgacgccgtg gccgacgtca     8460
aggaagtggc cgcttatgtg acgactgcgc gcggcgggca cggcgcggtg cgcgaagtcg     8520
cggagctgat cctgaaagcg cagggcaagt gggacgcgat gctctcgaag atccattgat     8580
tcatccgcat gacatccatc gacaaggaga tcgacatggg aaagatttca gcaccgaaaa     8640
acaaccgtga attcatcgag gcatgcgtca agtccggcga tgcggtccgg atcagacagg     8700
aagtggactg ggacaacgag gccggcgcca tcgtgcgccg cgcctgcgag ctcgccgaag     8760 ccgcccgtt catggagaac atcaaggact accccggctt cagctacttc ggcgcgccgc      8820
tgtcgaccta ccgccgcatg gcgatctcgc tcggcatgga cccggcatcg accttgccgc     8880
agatcggcgc cgagtacctc aaacgtacca acagcgagcc cgtggcgccg gtgatcgtcg     8940
acaaacggga cgccccgtgc aaggagaaca tcctgctcgg cgccgacgtc gatctgacca     9000
agctgccggt accgctggtc catgacggcg acggcggccg ctacgtcggc acctggcacg     9060
cggtgatcac caagcacccg gtgcgcggcg acgtgaactg gggcatgtac cggcagatga     9120
tgtgggacgg ccgcacgatg tcgggcgcc tgttcccgtt ctcggatctg ggcaaggcgc      9180
tcaccgagta ctacctgccg cgcggcgagg gctgccgtt cgcgaccgcg atcggcctgt      9240
cgccgctcgc cgcgatggcc gcctgcgcgc cctctccgat ccccgagccc gagctcaccg     9300
gcatgctcgc cggcgagccg gtgcgcctgg tgaagtgcga gaccaacgac ctcgaagtcc     9360
cggccgatgc cgagatcatc atcgagggcg tgatcctgcc cgactacaag gtcgaggaag     9420
gcccgttcgg cgaatacacc ggctaccgca ccagcccgcg cgacttccgc gtcaccttcc     9480
gcgtcgatgc gatcacctat cgcaacaacg cgacgatgac gatctcgaac atgggcgtgc     9540
cgcaggacga gggccagctg ctgcgctcgt tctcgctcgg gctcgaactc gagaagctgc     9600
tgaagagcca gggtatcccg gtgaccggcg tgtacatgca cccgcgctcg acccaccaca     9660
tgatgatcgt cggcgtgaag ccgacctacg ccggcatcgc gatgcagatc gcgcagctcg     9720
cgttcggctc caagctcggg ccgtggttcc acatggtgat ggtggtcgac gaccagaccg     9780
acatcttcaa ctgggacgag gtctatcacg cgttctgcac gcgctgcaat ccggagcgcg     9840
gcatccacgt gttcaagaac accaccggca ccgccctcta tccgcacgcc accccgcacg     9900
```

```
accgcaagta ctcgatcggc tcgcaggtgc tgttcgattg cctgtggccg gtcgattggg    9960
acaagaccaa cgacgtgccg acgctcgtca gcttcaagaa cgtctatccg aaggacatcc   10020
aggaaaaggt cacgaacaac tggaccgact acggcttcaa gccggtgaaa taaggagacg   10080
caacatgaac cagtgggaag tattcgtcat ggacccggcg gaactgccgg aaggcaagca   10140
gctcgagctg agcgtgcgca ccctcaaccc cgggctgaag aaatacacct atcagcgcgt   10200
cagggctgaa gtgtcacccg cgctcgacaa gttccccgac cagctccagg tccggctcgg   10260
gcgcggccga ctgagccccc agcgcttctc gatccgcatc atcgagaccg tccagcgcat   10320
gccggccaag tacctgtagt gacggcggac ggcgccgggc aactgcctct gcccggcgcc   10380
ggaagcgtga ccgccgcctt ttgtccgccc gcggcagcgc cgcggccggc actcaacccg   10440
ctaaagcatt gggggaacga tggcctattc cgatctgcgt gccttcctcg ccgacctcgg   10500
tgacgacttg ctgcgcatcc gcgatgagtt cgacccgcgc ttcgaagcgg cagccttgct   10560
ccgcaccctc cccgccgaag ggccggccgt gctgttcgag aacgtccgcg cctacccccgg  10620
cgcacgcatc gccggcaacc tgatcgccag ccgcagccgc ctggcgcgcg cactcggcac   10680
caccgccgac gcgctgccgc ggacctggct ggagcgcaag gagcacggca ttgcaccgat   10740
ccaggcgcgg gacgcggccc cggtcaaagg aagtgatcca ccgccatccg gacgatctgc   10800
tgtcgctgct gccgatcctg acccaccacg aaaaggatgc ggcccccttc atcaccaccg   10860
gcgtggtgtt gtgcaccgac cccgagaccg gccggcgcgg catgggcatc caccgcatga   10920
tggtcaaggg cgggcgccgg ctcggcatcc tgctcgccaa tccgccgatt ccgcatttcc   10980
tcgccaaggc cgaagcggcc ggcaagccgc tcgatgtcgc catcgcgctc ggtctcgaac   11040
ccgccaccct gctgtcgtcg gtggtcaagg tcggcccgcg ggtgcccgac aagatggccg   11100
ctgccggcgc cctgcgtggc gaaccggtcg agctggtgcg cgccgaaacg gtggatgtgg   11160
acatcccggc gcgcgccgaa atcgtcatcg aaggccggat tctgccgggc gtgcgcgaac   11220
tcgagggccc gttcggggag aacaccgggc actattttcc caacgtcagc ccggtcatcg   11280
agatcagcgc cgtcacccat cgcgacaact tcatctaccc gggcctgtgc ccatggtcgc   11340
ccgaggtcga tgcgctgctg tcgctggcgg ccggtgccga attgctcggc cagttgcagg   11400
ggctgatcga cggcgtcgtc gatctggaga tggccggcgg caccagcggc ttttccgtgg   11460
ttgtcgcagt ccatcggacc actgcggccg acgtcagacg gctggtcatg ctcgcgctca   11520
atctcgaccg ccgcctgaag acgatcaccg tcgtcgacga cgacgtcgac atccgcgacc   11580
cgcgcgaagt cgcctgggcc atggctaccc gctaccagcc cgcccgggac acggtcgtga   11640
tccacggctg cgaagcctat gtcatcgatc cttcggcgac cggggacggc acatcgaaag   11700
tcgggttcat cgccacccgt gccagcggcg cggactcgga ccgcatcacc ctgccgccgg   11760
cagcgctcgc gaaggcgcgc gccatcatcg ccagactgca ttgaacaggg agcaagccat   11820
gagaatcgtc gtcggaatgt ccggtgccag cggtgcgatc tacggcatcc ggatcctcga   11880
ggcactacag cgcatcggtg tcgaaaccga cctggtgatg tcggattcgg ccaagcggac   11940
catcgcatac gaaacggact attcgatcag cgacttgaag ggactcgcga cctgcgtcca   12000
tgacatcaat gatgtcgggg cgtcgatcgc cagcggctcg ttccgccatg ccggcatgat   12060
catcgcgccc tgttcgatca agaccctgtc cgcagtcgcc aactcgttca acacgaatct   12120
gttgatccgc gccgccgacg tcgcgttgaa ggagcggcgc aagctcgtgc tgatgctgcg   12180
cgagacgccg ctgcacctgg gccacctgcg cctgatgacc caggccacgg agaacggcgc   12240
ggttctcctc cctcccctgc ccgcgttcta ccaccgcccc aagacgctcg acgacatcat   12300
```

-continued

```
caaccagtcg gtgacgaaag tgctcgacca gttcgatctc gacgtcgatc tcttcgggcg    12360
gtggacgggc aacgaagaac gcgaactggc gaaatcccga taggacgctt ccgatgccac    12420
cgatcgccct tccctgtca ctcgaaggcg tcgtctgcac gggactcggt gcaggcgcgc     12480
agttcaccac cctcgactgg gtcgtcgatg aatgccggga aaagctcggc ttcatcccct    12540
ggcccggcac cttaacgtg aggacgcagg gcgcgcttgc gggcgtggac cgcacccgcc     12600
tcctgcgctc gggatacagc atccgcatcc ggccggcgcc cggctactgt gccgcggaat    12660
gcctcgtggt caacatcgcg gggcggatct ccggcgcggt gctattccca gaggtgcccg    12720
gctacccgga cggccagctc gaaatcatcg ctccggtgcc ggtacgaaga ccctcggcc     12780
tcaatgacgg cgaccgggtc aacctctcca tcggcatcag cacctccctt ttctgccggg    12840
cctgaacagt cgggagccgg caaacgtcag caaggagatt cacatggcac cgaagttctg    12900
cccgcaatgc ggcaccgccc tggtcctggc gacgatccat gggcgcgaac gtgaaacctg    12960
tccggcctgt ggcgaaacct ttttccacaa gcccgcgccc gtcgtgctgg cggtgatcga    13020
gcacgccggg caactcgtgc tgatccgccg caagctcgat ccgctcgccg gctactgggc    13080
accgccgggc ggctacgtcg aacgcggcga atcgctcgag gaggcggtcg tacgcgaggc    13140
gcgcgaggaa agcggactcg aggtcgccgt cgatgaactg atcggcgtgt attcgcaggc    13200
cgacgtgcgc gcggtgatcc tcgcctaccg cgcgcactcg atcggcggcg aaccggtcgc    13260
cggcgacgac gccggcgaga tctgcctcgt cgccccgggc cagctgccgg tgcagcgccc    13320
gccgcagagc ggcataccga tcgaacactg gtttttcagc gtagtggagg aagtcaccga    13380
tccatggaag tgggggcgcc gcaacagcgc caagaaaatg atgaggagat agaacgtgaa    13440
tatcatcgat acaccccga tcaccccga gatgccgcca aacctgctgg attacctgcg     13500
cggcggcgga cctgccctgc tgctgacgac gggcaccgac ggatacccga gctcggccta    13560
cacatgggca atcgccctcg acggcacgca cctgcgcttc ggcgcggacg agggcggctc    13620
cggctacgcc aacctggagc gcaccggaca ggccgcgata cacatcatcg gcccgaatga    13680
cctcgccttc ctcgtcaagg gaacggcacg tcttctcaag gcgcacatcg acactgcctc    13740
gcccgcgcgc atggcgctgt acgaactcga agtgatcgga gcccgcgatc agtccttccc    13800
cggcgtcacg gccaagccct tcacctatga atggccggcg gcgcagcgcg cggcgctgac    13860
gaagatggaa cagtcggtgt ttaccgaaat gcgcgaattc gcccagtgac aaaggccgca    13920
cgctcctgga ccccccattc aaaccttcag gaatttctc atgtcgtatt tcgaccagac     13980
caccgaaacc cttccccgcg aacgcctggc cgccctgcag ttcgacaagc tgcaggcgat    14040
gatgaacgag ctgtggggca ggaaccgctt ctacaccaac aagtggaaag ccgccggcgt    14100
cgaaccgggt gacatccgga cgctcgacga tctgcgcacc aactacgaag tcggcaacac    14160
ccaggccgtg ctcgacggcg acctcgacga cttcatcgcg gcaagcctga gcagggcgt    14220
ctgatccgct ggcgccgccc ctgcaggcgg gcggcgaatc ggttccgccg gc           14272
```

<210> SEQ ID NO 24
<211> LENGTH: 42
<212> TYPE: PRT
<213> ORGANISM: Thauera aromatica

<400> SEQUENCE: 24

Gly Lys Ile Ser Ala Pro Lys Asn Asn Arg Glu Phe Ile Glu Ala Ser
 1               5                  10                  15

Val Lys Ser Gly Asp Ala Val Arg Ile Arg Gln Glu Val Asp Trp Asp

-continued

```
                    20                  25                  30

Asn Glu Ala Gly Ala Ile Val Arg Arg Ala
            35                  40

<210> SEQ ID NO 25
<211> LENGTH: 26
<212> TYPE: PRT
<213> ORGANISM: Thauera aromatica

<400> SEQUENCE: 25

Met Gly Lys Ile Ser Ala Pro Lys Asn Asn Arg Glu Phe Ile Glu Ala
  1               5                  10                  15

Cys Val Lys Ser Gly Asp Ala Val Arg Ile
                20                  25

<210> SEQ ID NO 26
<211> LENGTH: 38
<212> TYPE: PRT
<213> ORGANISM: Thauera aromatica

<400> SEQUENCE: 26

Met Asp Leu Arg Tyr Phe Ile Asn Gln Xaa Ala Glu Ala His Glu Leu
  1               5                  10                  15

Lys Arg Ile Thr Thr Glu Val Asp Trp Asn Leu Glu Ile Ser His Val
                20                  25                  30

Ser Lys Leu Xaa Xaa Glu
            35

<210> SEQ ID NO 27
<211> LENGTH: 38
<212> TYPE: PRT
<213> ORGANISM: Thauera aromatica

<400> SEQUENCE: 27

Met Asp Leu Arg Tyr Phe Ile Asn Gln Cys Ala Glu Ala His Glu Leu
  1               5                  10                  15

Lys Arg Ile Thr Thr Glu Val Asp Trp Asn Leu Glu Ile Ser His Val
                20                  25                  30

Ser Lys Leu Thr Glu Glu
            35

<210> SEQ ID NO 28
<211> LENGTH: 33
<212> TYPE: PRT
<213> ORGANISM: Thauera aromatica

<400> SEQUENCE: 28

Met Lys Phe Pro Val Pro His Asp Ile Gln Ala Lys Thr Ile Pro Gly
  1               5                  10                  15

Thr Glu Gly Trp Glu Arg Met Tyr Pro Xaa Xaa Xaa Ala Phe Val Xaa
                20                  25                  30

Asp

<210> SEQ ID NO 29
<211> LENGTH: 33
<212> TYPE: PRT
<213> ORGANISM: Thauera aromatica

<400> SEQUENCE: 29

Met Lys Phe Pro Val Pro His Asp Ile Gln Ala Lys Thr Ile Pro Gly
  1               5                  10                  15
```

```
Thr Glu Gly Trp Glu Arg Met Tyr Pro Tyr His Tyr Gln Phe Val Thr
            20                  25                  30
Asp

<210> SEQ ID NO 30
<211> LENGTH: 7
<212> TYPE: PRT
<213> ORGANISM: Thauera aromatica

<400> SEQUENCE: 30

Met Gln Met Leu Asp Asp Lys
 1               5

<210> SEQ ID NO 31
<211> LENGTH: 28
<212> TYPE: PRT
<213> ORGANISM: Thauera aromatica

<400> SEQUENCE: 31

Gly Gln Gln Ala Glu Phe Leu Met Ala Xaa Xaa Xaa Xaa Xaa Pro Val
 1               5                  10                  15

Xaa Ala Gly Ala Glu Ile Val Leu Glu Xaa Gly Ile
            20                  25

<210> SEQ ID NO 32
<211> LENGTH: 21
<212> TYPE: DNA
<213> ORGANISM: Primer

<400> SEQUENCE: 32
atggayctsc gstacttcat c                                         21

<210> SEQ ID NO 33
<211> LENGTH: 20
<212> TYPE: DNA
<213> ORGANISM: Primer

<400> SEQUENCE: 33
ttrtcrtcsa gcatctgcat                                           20

<210> SEQ ID NO 34
<211> LENGTH: 21
<212> TYPE: DNA
<213> ORGANISM: Primer

<400> SEQUENCE: 34
catsaggaay tcsgcctgct g                                         21

<210> SEQ ID NO 35
<211> LENGTH: 22
<212> TYPE: DNA
<213> ORGANISM: Primer

<400> SEQUENCE: 35
cgggatatca ctcagcataa tg                                        22

<210> SEQ ID NO 36
<211> LENGTH: 20
<212> TYPE: DNA
<213> ORGANISM: Primer

<400> SEQUENCE: 36
```

-continued aattaaccct cactaaaggg                      20

<210> SEQ ID NO 37
<211> LENGTH: 17
<212> TYPE: DNA
<213> ORGANISM: Primer

<400> SEQUENCE: 37
gacaacttcg tcgtcaa                         17

<210> SEQ ID NO 38
<211> LENGTH: 20
<212> TYPE: DNA
<213> ORGANISM: Primer

<400> SEQUENCE: 38
gtggatattg gcttcggaaa                      20

<210> SEQ ID NO 39
<211> LENGTH: 18
<212> TYPE: DNA
<213> ORGANISM: Primer

<400> SEQUENCE: 39
tcgccggcga cgacgccg                        18

<210> SEQ ID NO 40
<211> LENGTH: 18
<212> TYPE: DNA
<213> ORGANISM: Primer

<400> SEQUENCE: 40
ccgcgcgctg cgccgccg                        18

<210> SEQ ID NO 41
<211> LENGTH: 10
<212> TYPE: PRT
<213> ORGANISM: Thauera aromatica

<400> SEQUENCE: 41

Met Glu Gln Ala Lys Asn Ile Lys Leu Val
 1               5                  10

<210> SEQ ID NO 42
<211> LENGTH: 10
<212> TYPE: PRT
<213> ORGANISM: Thauera aromatica

<400> SEQUENCE: 42

Met Glu Gln Ala Lys Asn Ile Lys Leu Val
 1               5                  10

<210> SEQ ID NO 43
<211> LENGTH: 10
<212> TYPE: PRT
<213> ORGANISM: Thauera aromatica

<400> SEQUENCE: 43

Met Arg Ile Val Val Gly Met Xaa Gly Ala
 1               5                  10

<210> SEQ ID NO 44
<211> LENGTH: 10
<212> TYPE: PRT

-continued

```
<213> ORGANISM: Thauera aromatica

<400> SEQUENCE: 44

Met Arg Ile Val Val Gly Met Ser Gly Ala
  1               5                  10
```